US012746404B2

(12) United States Patent
Wasserman et al.

(10) Patent No.: US 12,746,404 B2
(45) Date of Patent: Sep. 29, 2026

(54) METHODS OF PRODUCING AN ELECTRODE ARRAY

(71) Applicant: Novocure GmbH, Root (CH)

(72) Inventors: Yoram Wasserman, Haifa (IL); Stas Obuchovsky, Haifa (IL); Nataliya Kuplennik, Haifa (IL)

(73) Assignee: Novocure GmbH, Baar (CH)

( * ) Notice: Subject to any disclaimer, the term of this patent is extended or adjusted under 35 U.S.C. 154(b) by 538 days.

(21) Appl. No.: 17/693,879

(22) Filed: Mar. 14, 2022

(65) Prior Publication Data

US 2022/0288405 A1 Sep. 15, 2022

Related U.S. Application Data

(60) Provisional application No. 63/230,310, filed on Aug. 6, 2021, provisional application No. 63/168,689, filed
(Continued)

(51) Int. Cl.
*A61N 1/04* (2006.01)
*A61N 1/40* (2006.01)
(Continued)

(52) U.S. Cl.
CPC .............. *A61N 1/40* (2013.01); *A61N 1/0476* (2013.01); *A61N 1/06* (2013.01); *B81C 1/00166* (2013.01);
(Continued)

(58) Field of Classification Search
CPC .......... A61N 1/40; A61N 1/0476; A61N 1/06; A61N 1/36002; A61N 1/0496; G01N 27/3272; B81C 1/00166; Y10T 29/49222
See application file for complete search history.

(56) References Cited

U.S. PATENT DOCUMENTS 4,722,761 A 2/1988 Cartmell et al.
4,846,196 A * 7/1989 Wiksell .................... A61N 1/06 600/549
(Continued)

FOREIGN PATENT DOCUMENTS

CN 107456653 A 12/2017
EP 0319711 A1 6/1989
(Continued)

OTHER PUBLICATIONS

Khmelnitskiy et al, "Soft ionic electroactive polymer actuators and sensors with graphene/polyaniline nanocomposite electrodes," 2018 IEEE Conference of Russian Young Researchers in Electrical and Electronic Engineering, Moscow and St. Petersburg, Russia, 2018, pp. 419-422. (Year: 2018).*
(Continued)

*Primary Examiner* — A. Dexter Tugbang
(74) *Attorney, Agent, or Firm* — DUNLAP CODDING, P.C.

(57) ABSTRACT

A method of making a transducer array comprises providing an electrode layer having a plurality of electrode elements configured to receive an electrical signal from an electric field generator producing an electric signal as a Tumor Treating Field (TTField), applying conductive gel elements in a flowable state to the plurality of electrode elements; and, curing the conductive gel elements on the electrode elements.

21 Claims, 20 Drawing Sheets

Related U.S. Application Data on Mar. 31, 2021, provisional application No. 63/160,174, filed on Mar. 12, 2021.

(51) Int. Cl.

| | |
|---|---|
| ***B81C 1/00*** | (2006.01) |
| ***G01N 27/327*** | (2006.01) |
| *A61N 1/06* | (2006.01) |

(52) U.S. Cl.

CPC ..... *G01N 27/3272* (2013.01); *Y10T 29/49222* (2015.01)

(56) References Cited

U.S. PATENT DOCUMENTS

| | | | | |
|---|---|---|---|---|
| 6,263,226 | B1 | 7/2001 | Axelgaard et al. | |
| 2007/0123765 | A1 * | 5/2007 | Hetke | A61N 1/0476 600/378 |
| 2013/0118899 | A1 * | 5/2013 | Chen | G01N 27/3272 204/403.02 |
| 2013/0325096 | A1 | 12/2013 | Dupelle et al. | |
| 2020/0171297 | A1 | 6/2020 | Kirson et al. | |
| 2020/0298001 | A1 | 9/2020 | Muller et al. | |
| 2021/0198714 | A1 * | 7/2021 | Pirmoradi | G01N 27/3272 |

FOREIGN PATENT DOCUMENTS

| | | | | |
|---|---|---|---|---|
| JP | 02-035751 | U | 8/1988 | |
| JP | 2013202336 | A * | 10/2013 | |
| WO | WO-2019100016 | A1 * | 5/2019 | A61N 1/40 |
| WO | WO 2019/124566 | A1 | 6/2019 | |
| WO | WO 2020/110050 | A1 | 6/2020 | |

OTHER PUBLICATIONS

Liu et al., "Disruption of Tumor Neovasculature by Microbubble Enhanced Ultrasound: A Potential New Physical Therapy of Anti-Angiogenesis", Ultrasound in Medicine & Biology, vol. 38, No. 2, pp. 253-261, Feb. 2012. (Year: 2012).*

International Searching Authority, Notification of Transmittal of the International Search Report and the Written Opinion (PCT/IB2022/052182), dated Sep. 7, 2022, 15 pages.

Japan Intellectual Property Office; Office Action regarding Japanese Patent Application No. 2023-555816, issued Nov. 4, 2025, with English summary.

Taiwan Intellectual Property Office, Office Action regarding Patent Application No. 111109097, May 26, 2026, and English Translation.

China National Intellectual Property Administration, Office Action regarding Application No. 202280020930.6 dated Apr. 18, 2026 (7 pages), with English Machine Translation.

* cited by examiner

200

202: Support layer positioned on skin facing side of electrode elements

↓

204: Gel dispensed on at least a portion of the support layer and cured forming a conductive gel layer

METHODS OF PRODUCING AN ELECTRODE ARRAY

CROSS REFERENCE TO RELATED APPLICATIONS AND INCORPORATION BY REFERENCE STATEMENT

The present patent application claims priority to the provisional patent applications identified by U.S. Ser. No. 63/160,174, entitled "Hydrogel-Electrode Assemblies and Methods of Production and Use thereof," filed on Mar. 12, 2021; U.S. Ser. 63/168,689, entitled "Electrode Array and Methods of Production and Use thereof," filed on Mar. 31, 2021; and, U.S. Ser. No. 63/230,310, entitled "Electrode Array and Methods of Production and Use thereof," filed on Aug. 6, 2021, the entire contents of which are hereby incorporated by reference.

BACKGROUND

Tumor Treating Fields (TTFields or TTFs) are low intensity (e.g., 1-3 V/cm) alternating electric fields within the intermediate frequency range (100-500 kHz) targeting solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776, each of which is hereby incorporated by reference in their entirety.

TTFields are typically delivered through two pairs of transducer arrays that generate perpendicular fields within the treated tumor. The transducer arrays that make up each of these pairs are positioned on opposite sides of the body part that is being treated. For example, in using the OPTUNE® system (manufactured by Novocure Limited, having a principle place of business in St. Helier, Jersey), at least one pair of electrodes of the transducer array is located to the left and right (LR) of the tumor, and at least one pair of electrodes is located anterior and posterior (AP) to the tumor.

Each transducer array used for the delivery of TTFields in the OPTUNE® system comprises at least one set of non-conductive ceramic disk electrodes coupled to the patient's skin. For example, the OPTUNE® system may position the transducer arrays on a patient's shaved head (e.g., treatment of Glioblastoma, hereinafter 'GBM') with the non-conductive ceramic disk electrodes coupled to the patient's skin through a layer of conductive medical gel.

To form the ceramic disk electrodes, a conductive layer is formed on a top surface of nonconductive ceramic material. A bottom surface of the nonconductive ceramic material is coupled to the conductive medical gel. The nonconductive ceramic material is a safety feature to ensure that direct-current signals are blocked from unintentionally being transmitted to the patient. By interposing a nonconductive ceramic material between the conductive layer and the conductive medical gel, the prior art system was thought to ensure the patient remains protected. The medical gel may deform to match the body's contours and provide electrical contact between the arrays and the skin; as such, the medical gel interface bridges the skin and reduces interference. The device is intended to be continuously worn by the patient for two to four days before removal for hygienic care and re-shaving (if necessary), followed by reapplication with a new set of arrays. As such, the medical gel remains in substantially continuous contact with an area of the patient's skin for a period of 2-4 days at a time. Further, there may only be a brief period of time in which the area of skin is uncovered and exposed to the environment before more medical gel is applied thereto.

Conventionally, the medical gel is applied manually to the electrode elements, which is a labor-intensive, tedious and expensive procedure. Further, the medical gel has a tendency to move laterally on the patient.

As such, new and improved array assemblies, and methods of making the array assemblies that speed up manufacturing and anchor the medical gel to the electrode arrays to reduce lateral movement of the medical gel is desired. It is to such assemblies and methods of producing and using the same, that the present disclosure is directed.

DETAILED DESCRIPTION

Figure 1:
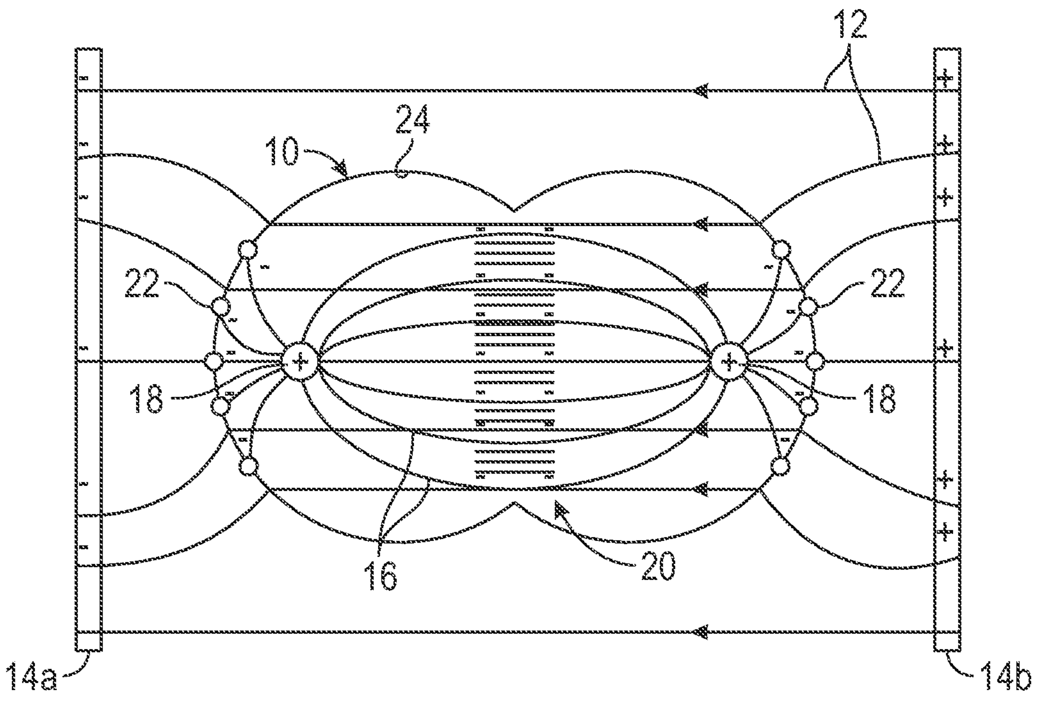
FIG. 1 is an exemplary embodiment of a schematic diagram of electrodes applied to living tissue.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "liquid hydrogel" and "flowable hydrogel" as used herein may be understood to refer to an uncured hydrogel formulation that is in an at least partially flowable form. That is, the term "liquid hydrogel" refers to a hydrogel formulation prior to curing and that is curable by ultraviolet (UV) radiation or ionizing high energy radiation.

Referring now to the drawings and in particular to FIG. 1, shown therein is an exemplary embodiment of a dividing cell 10, under the influence of external TTFields 12. In some embodiments, external TTFields may include alternating fields 12 in the frequency range of about 100 KHZ to about 300 KHZ. In some embodiments, TTFields may include alternating fields 12 in the frequency range of about 50 KHZ to about 500 KHZ. In some embodiments, the TTFields may include alternating fields 12 in the frequency range of about 50 KHz to about 1 MHz. Fields 12 may be generated by a first electrode 14*a* connecting to the negative output of the electric field generator 32 and a second electrode 14*b* connected to the positive output. Microtubules 16, as well as other polar macromolecules within the dividing cell 10 or surrounding the dividing cell 10, may have strong dipole moment providing susceptibility to such TTFields 12. Positive outputs of the microtubules 16 may be positioned at centrioles 18. At least one negative pole may be positioned at a center 20 of the dividing cell 10 and at least one negative pole may be positioned at a point of attachment 22 of the microtubules 16 to a cell membrane 24 of the dividing cell 10. The locations of the positive outputs and the negative outputs form at least one set of double dipoles. The at least one set of double dipoles may provide susceptibility to TTFields 12 of differing directions. As used herein, the alternating electric field may be referred to as the electric field or the TTField 12. The TTField 12 may be a frequency specific, alternating electric field that is applied to the site of a tumor in the body. In some embodiments, one or more electrical fields may be applied to the dividing cell 10 in order to increase the permeability of the membrane of the dividing cell 10. For example, one or more electrical fields may be applied to the dividing cell 10 in order to increase the permeability of the membrane of the dividing cell 10 such that one or more chemicals, drugs, DNA and/or chromosomes may be introduced into the dividing cells (i.e., via electroporation).

Figure 2:
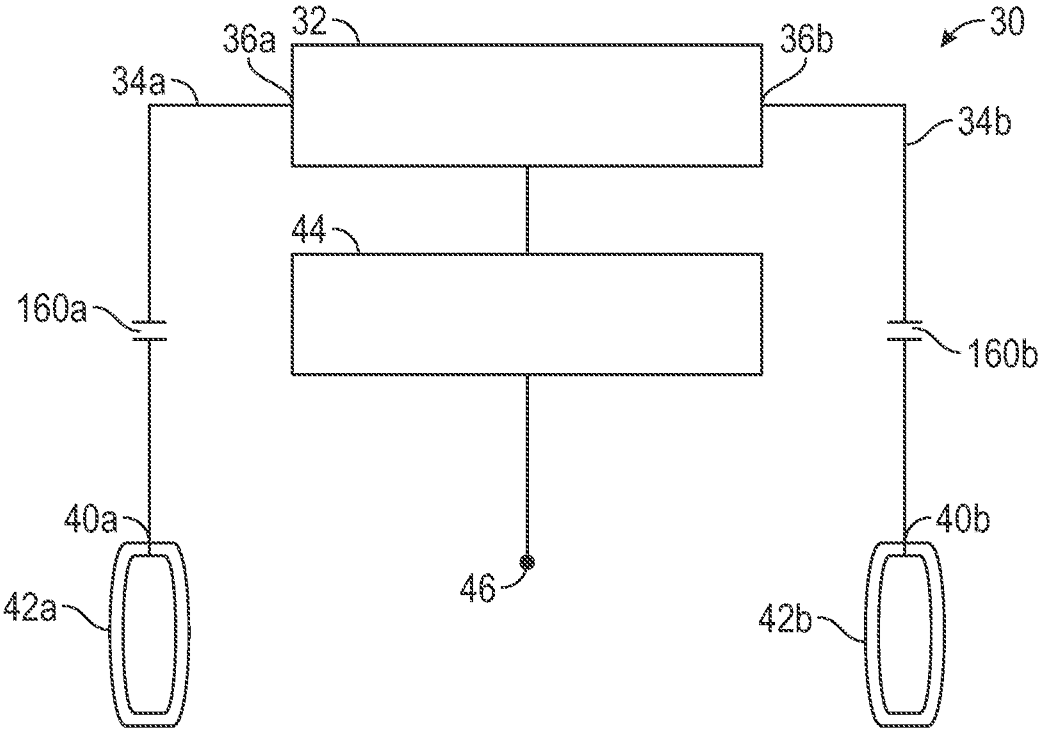
FIG. 2 is an exemplary embodiment of an electronic device configured to generate a TTField.

FIG. 2 illustrates a schematic diagram of an exemplary electronic apparatus 30 configured to generate TTFields 12 in accordance with the present disclosure. The TTFields 12 described may be capable of destroying one or more tumor cells. The specifications of the electronic apparatus 30 as a whole and/or individual components of the electronic apparatus 30 as described herein may be influenced by living systems behaving according to "Ohmic" properties, rather than dielectric properties, at the frequency of the TTFields (e.g., 50 KHZ-500 KHZ or 50 KHZ-1 MHZ).

Generally, the electronic apparatus 30 may include an electric field generator 32 and two or more conductive leads 34. For example, in FIG. 2, the electronic apparatus includes a first conductive lead 34*a* and a second conductive lead 34*b*. The first conductive lead 34*a* includes a first end 36*a* and a second end 40*a*. The first end 36*a* of the first conductive lead 34*a* is conductively attached to the electric field generator 32 and the second end 40*a* of the first conductive lead 34*a* is connected to a first pad 42*a*. Similarly, the second conductive lead 34*b* includes a first end 36*b* and a second end 40*b*. The first end 36*b* of the second conductive lead 34*b* is conductively attached to the electric field generator 32 and the second end 40*b* of the second conductive lead 34*b* is connected to a second pad 42*b*. The first pad 42*a* and the second pad 42*b* may also be referred to as electrodes, such as the first electrode 14*a* or the second electrode 14*b*, or electrode pad.

The electric field generator 32 is configured to provide one or more electric signals (TTFields signals) in the shape of waveforms and/or trains of pulses as an output. Each pad 42*a* and 42*b* are provided with a potential difference by the electric signals (e.g., waveforms) that generate a current when the pads 42*a* and 42*b* are attached to a body by the electric signals (e.g., wave forms). As each of the first pad 42*a* and the second pad 42*b* is provided with the electric signals having a frequency and an amplitude, an electrical current will flow between the first pad 42*a* and the second pad 42*b* when the first pad 42*a* and the second pad 42*b* are applied on a conductive material, such as a human body.

The electric field generator 32 may be configured to generate an alternating voltage wave form at frequencies in the range from about 50 KHZ to about 1 GHz, and ranges within (i.e., from about 50 KHz to about 1 mHz, from about 50 KHz to about 500 KHz). In some embodiments, the electric field generator 32 is configured to generate an alternating voltage wave form at frequencies in the range of about 100 KHZ to about 300 KHZ (i.e., the TTFields). The voltages are such that an electric field intensity in tissue within the treatment area is in the range of about 0.1 V/cm to about 10V/cm. To achieve this field, the potential difference between the two conductors 14, (i.e. electrode element 82 described in detail below and shown in FIG. 4) in each of the first pad 42*a* or second pad 42*b* may be determined by the relative impedances of the body.

In some embodiments, the first pad 42*a* and the second pad 42*b* may be configured to generate an alternating electric field within a target region of a patient. The target region may comprise, for example, at least a portion of a tumor. Generation of the alternating electric field may be configured to selectively destroy and/or inhibit growth of at least a portion of the tumor. The alternating electric field may be generated at any frequency capable of selectively destroying and/or inhibiting growth of at least a portion of the tumor. For example (but not by way of limitation), the alternating electric field may have a frequency within the range of about 50 kHz to about 1 mHz, as well as a range formed from any values within (i.e., a range of from about 50 kHz to about 1 mHz, a range of from about 100 kHz to about 150 kHz, a range of from about 150 kHz to about 300 kHz, etc.), and a range that combines two integers that fall between two of the above-referenced values (i.e., a range of from about 32 kHz to about 333 kHz, a range of from about 78 kHz to about 298 kHz, etc.).

In some embodiments, the alternating electric field may be configured to be imposed at two or more different frequencies. In some embodiments, each of the two or more different frequencies may be selected from any of the above-referenced values, or a range formed from any of the above-referenced values, or a range that combines two integers that fall between two of the above-referenced values.

In some embodiments, the first pad 42*a* and the second pad 42*b* (i.e., a pair of pads) may be configured differently depending upon the application in which the pair of pads 42*a* and 42*b* are to be used. In some embodiments, the pair of pads 42*a* and 42*b* may be externally applied to a patient (e.g., applied to an epidermis layer of skin of a patient) with the generation of the electric field (TTField) provided within tissue of the patient. Generally, each of the first pad 42*a* and the second pad 42*b* is placed on the epidermis of the skin of the patient by a user such that the electric field is configured to generate across tissue of a patient within a predetermined treatment area. TTFields that are applied externally can be of a local type or widely distributed type, for example, the treatment of skin tumors and treatment of lesions close to the skin surface.

In some embodiments, the user may be a medical professional, such as a doctor, nurse, therapist, or other person acting under the instruction of a doctor, nurse, or therapist.

In some embodiments, the user may be the patient, that is, the patient may place the pads 42*a* and 42*b* on the epidermis layer within a predetermined treatment area.

In some embodiments, the electronic apparatus 30 may optionally include a control box 44 and one or more temperature sensor 46 coupled to the control box 44. In some embodiments, multiple temperature sensors 46 may be positioned to sense temperature at the predetermined treatment area. The one or more temperature sensor 46 may include, but are not limited to, thermistors, thermocouples, RTDs, integrated circuit temperature sensors such as the Analog Devices AD590 and the Texas Instruments LM135, and/or combinations thereof. It is contemplated that any temperature sensor 46 known within the art may be used if configured to provide an accurate and/or precise temperature reading of the predetermined treatment area. The control box 44 may be configured to control amplitude of the electric field so as not to generate excessive heating in the treatment area.

In some embodiments, the control box 44 may be configured to control output of the electric field generator 32. For example, in some embodiments, the control box 44 may be configured to control output of the electric field generator 32 such that output remains constant at a value preset by a user. In some embodiments, the control box 44 may be configured to set output of the electric field generator 32 at a maximal value, with the maximal value configured such that excessive heat is not provided at the predetermined treatment area. In some embodiments, the control box 44 may be configured to provide one or more feedback indicators. For example, the control box 44 may be configured to provide a feedback indicator (e.g., sound, light) when a temperature of the predetermined treatment area (as sensed by temperature sensor 746) exceeds a preset limit.

In some embodiments, the control box 44 may be configured to control output of the electric field generator 32 based on one or more readings of the temperature sensor 46. In some embodiments, one or more temperature sensor 46 may be connected to and/or otherwise associated with the first pad 42*a* or the second pad 42*b* and configured to sense temperature of the epidermis and/or treatment area at either one or both of the first pad 42*a* or the second pad 42*b*.

In some embodiments, one or more of the conductive leads 34 may be standard isolated conductors having a flexible metal shield. In some embodiments, the flexible metal shield may be grounded to prevent spread of any electric field generated by the one or more conductive leads 34.

Pads 42*a* and 42*b* may be shaped, sized and positioned to generate the TTField configuration, direction and intensity at the treatment area. To that end, the pads 42*a* and 42*b* may be square, rectangular, circular, oval, or any fanciful shape.

Figure 3A:
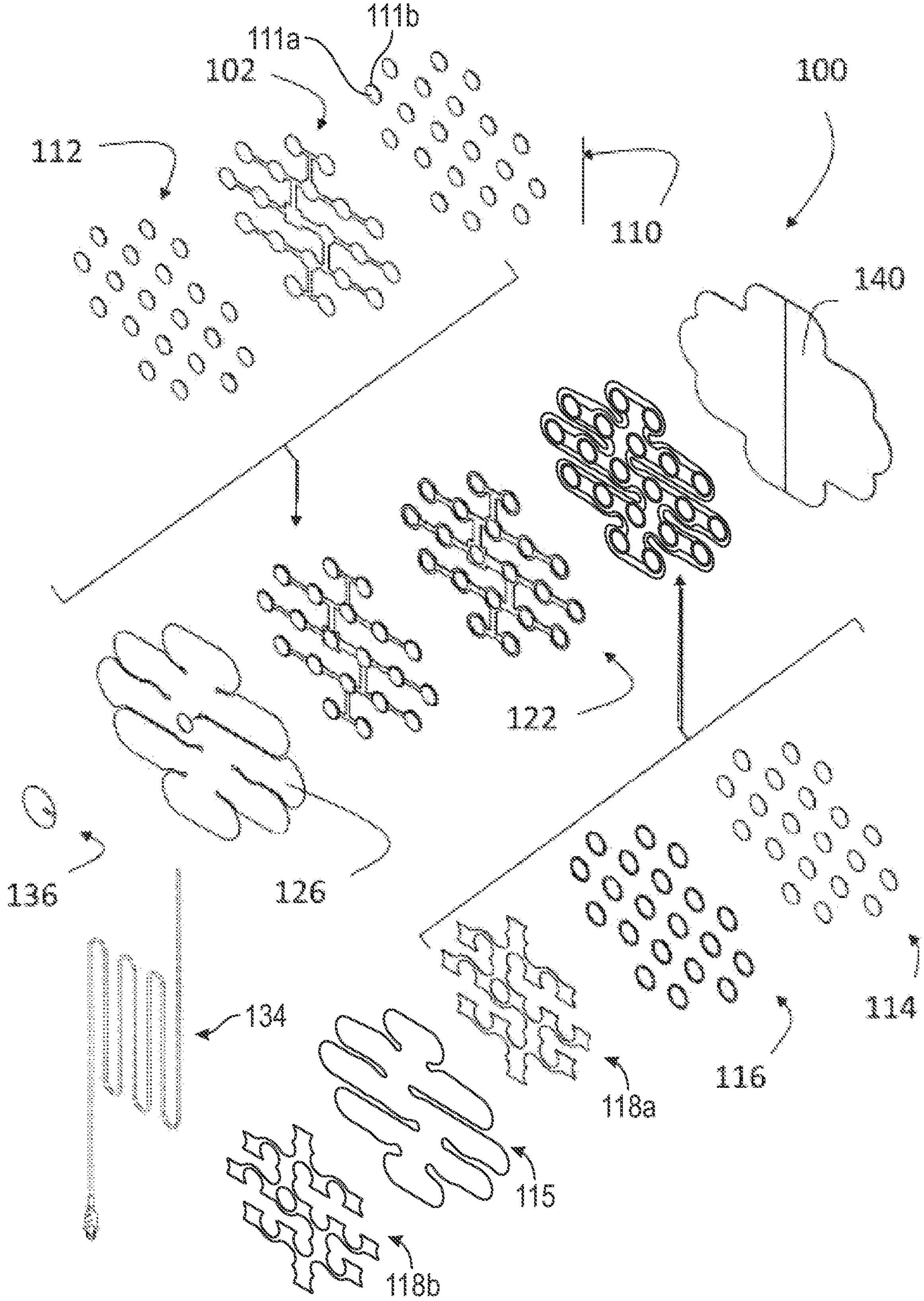
FIG. 3A is an exploded view of one embodiment of a transducer array that has a first layout of electrode elements.
Figure 3B:
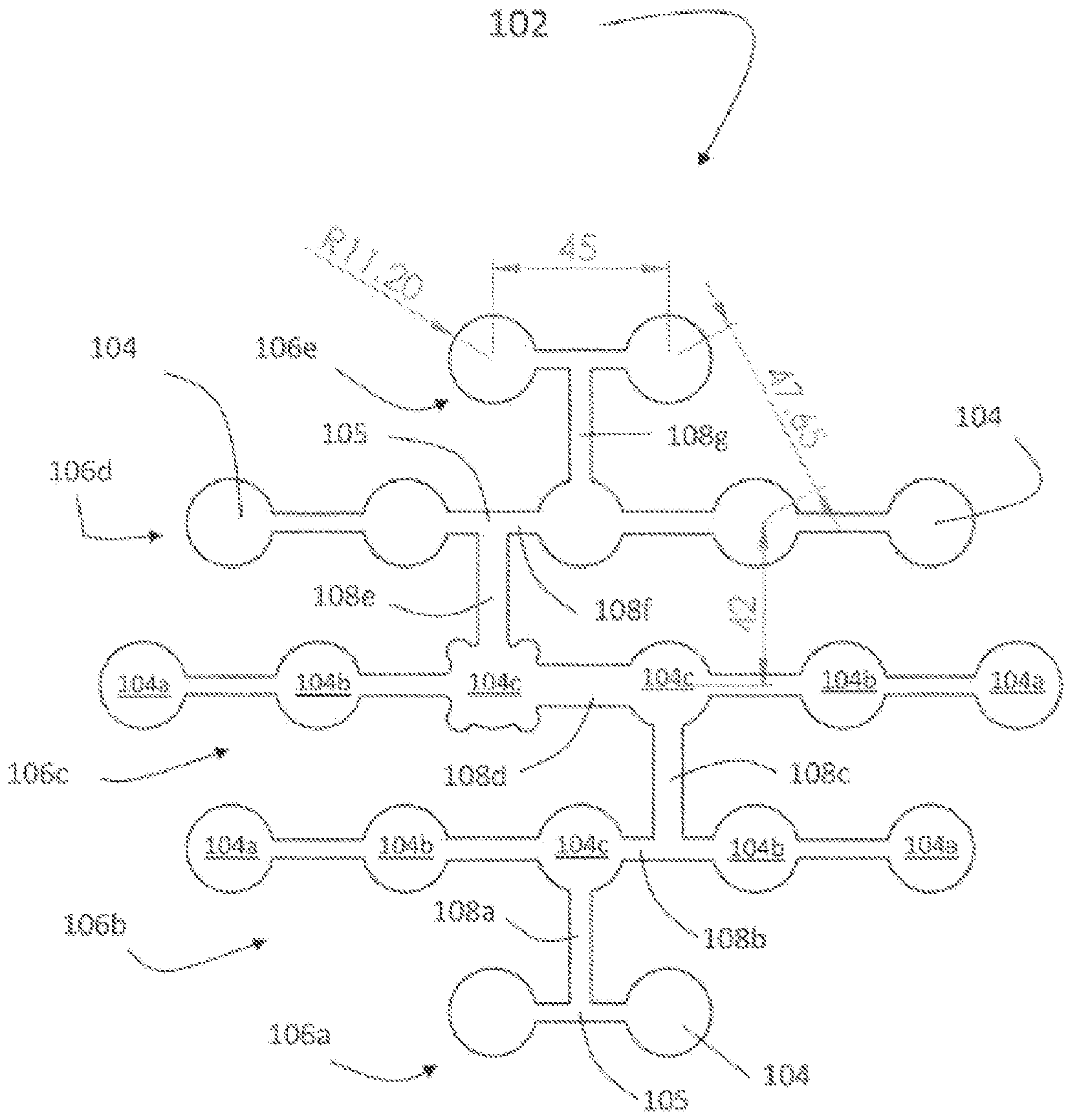
FIG. 3B is a plan view of a flex circuit used in the transducer array illustrated in FIG. 3A.
Figure 3C:
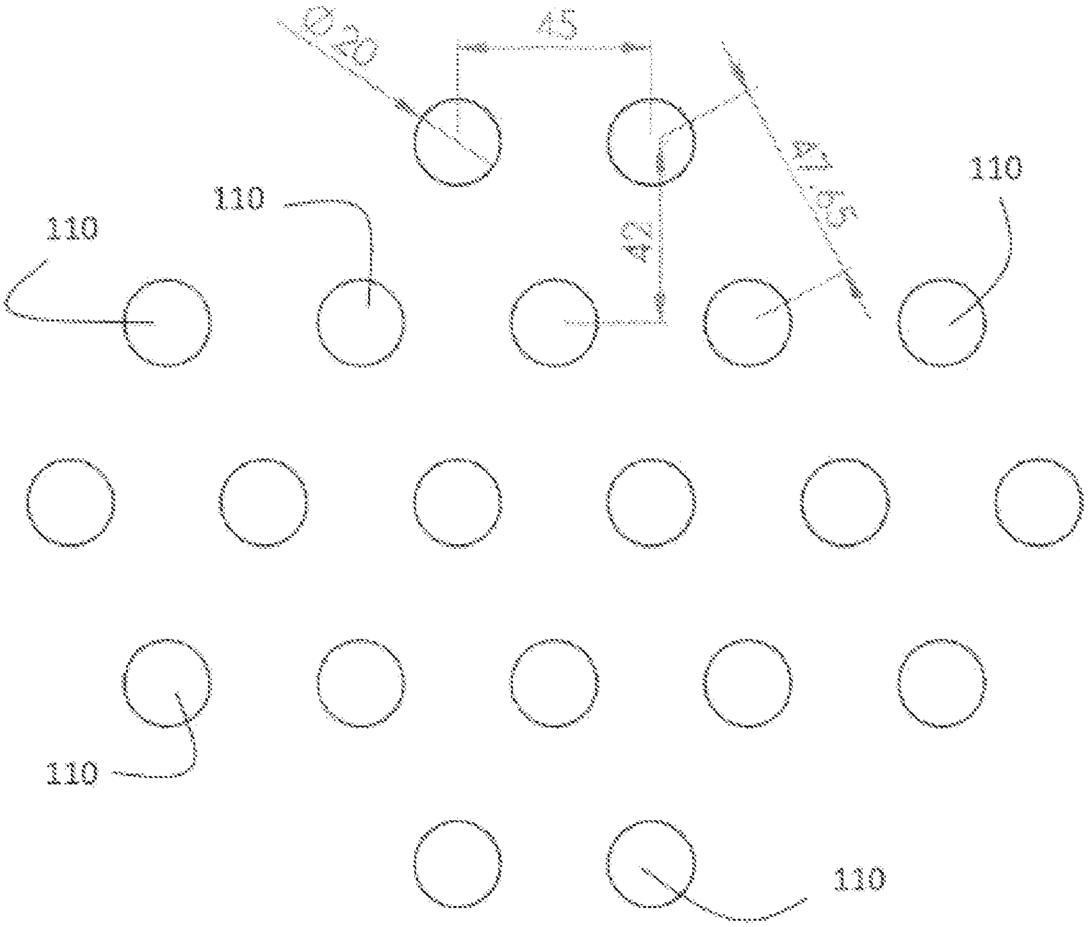
FIG. 3C is a plan view of electrode elements used in the transducer array illustrated in FIG. 3A.
Figure 3D:
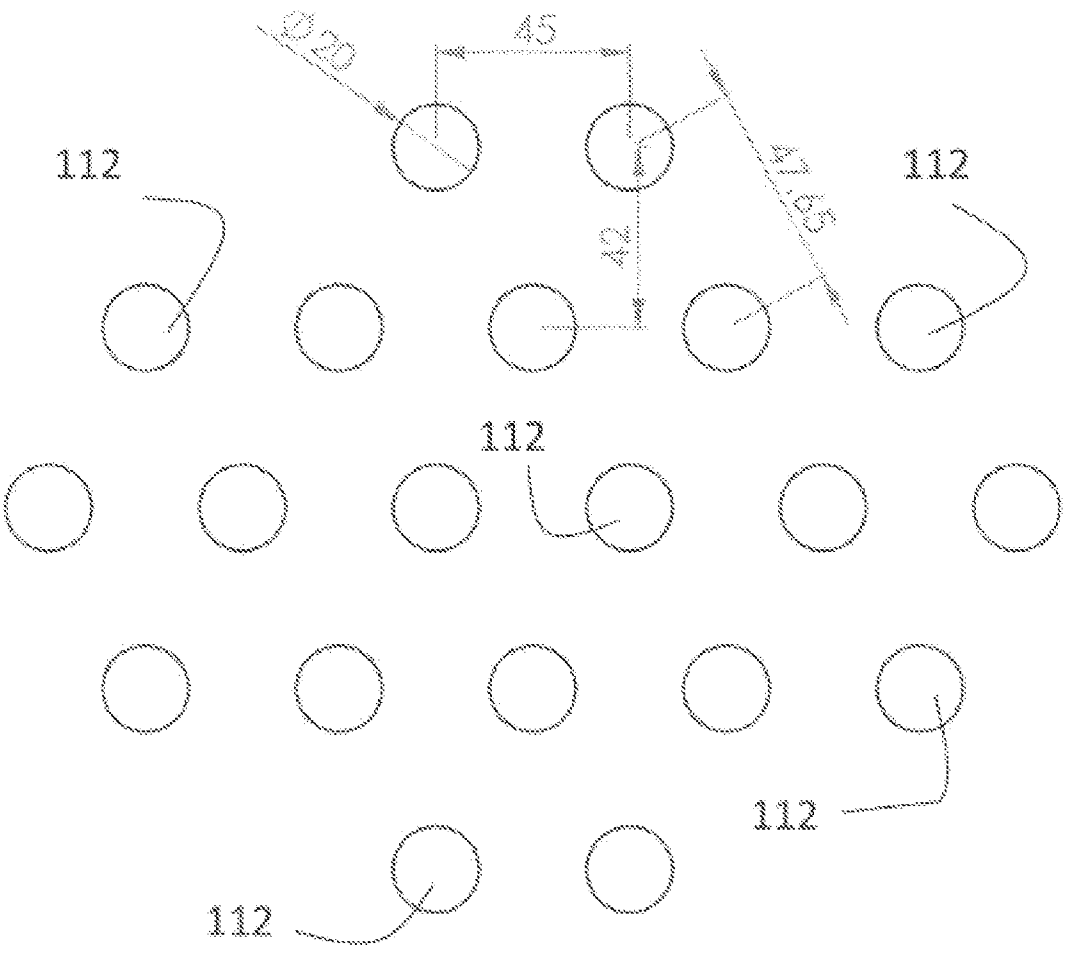
FIG. 3D is a plan view of stiffeners used in the transducer array illustrated in FIG. 3A.
Figure 3E:
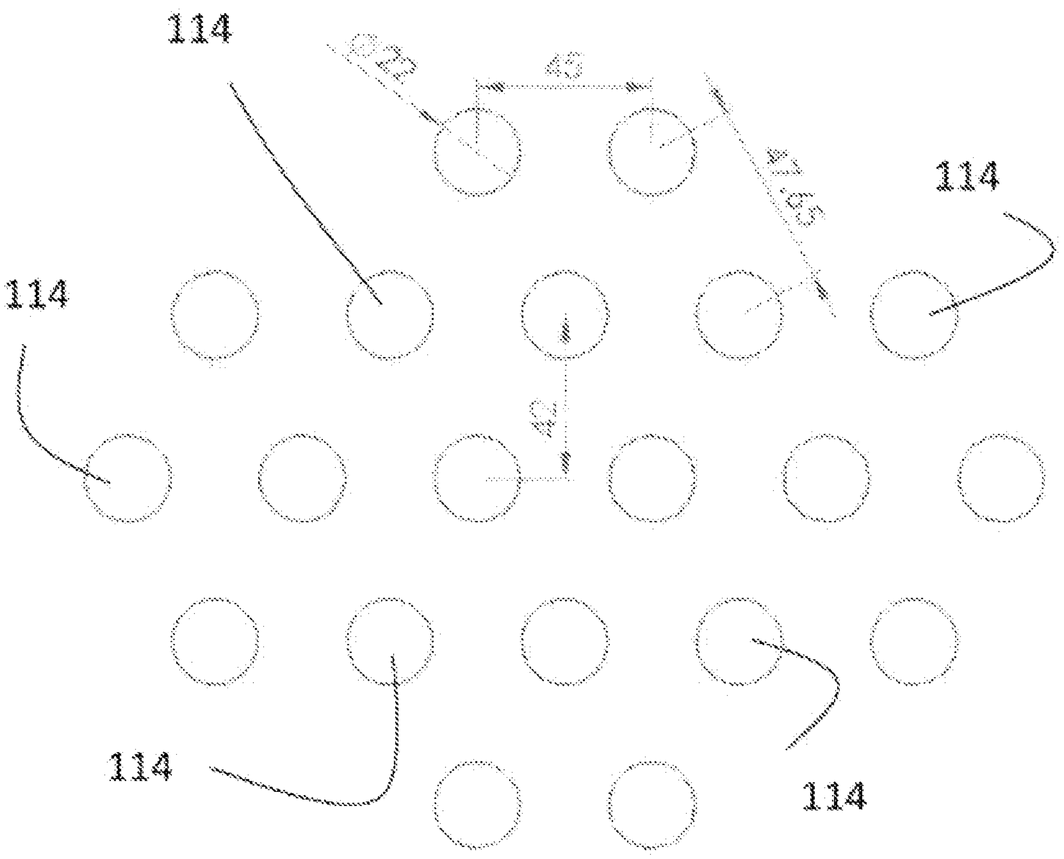
FIG. 3E is a plan view of conductive hydrogel discs used in the transducer array illustrated in FIG. 3A.
Figure 3F:
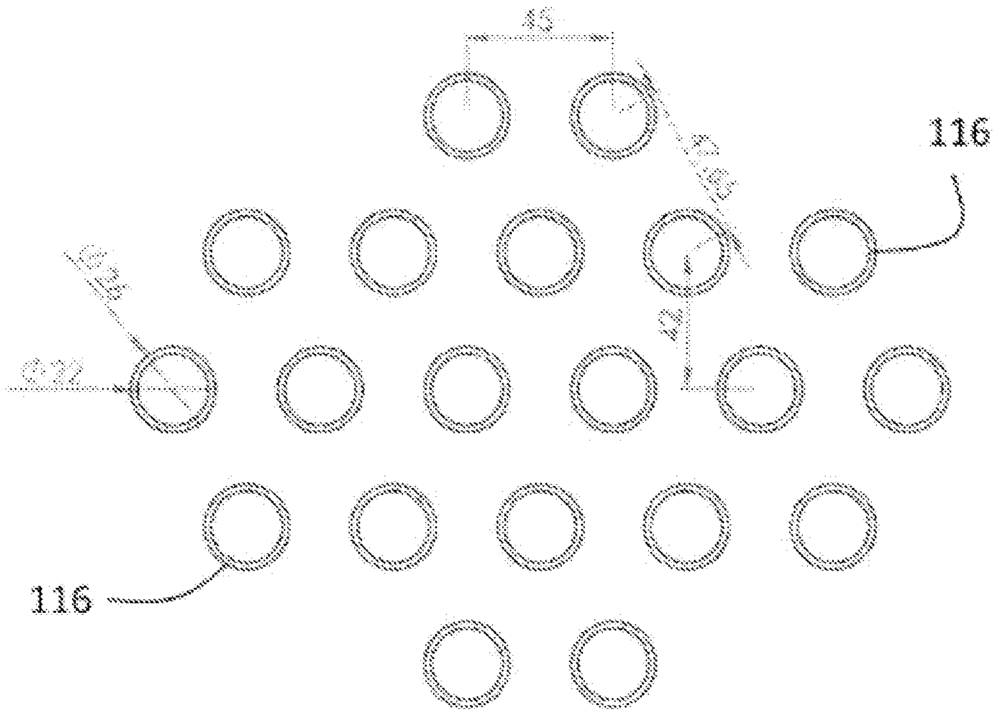
FIG. 3F is a plan view of hydrogel barriers used in the transducer array illustrated in FIG. 3A.
Figure 3G:
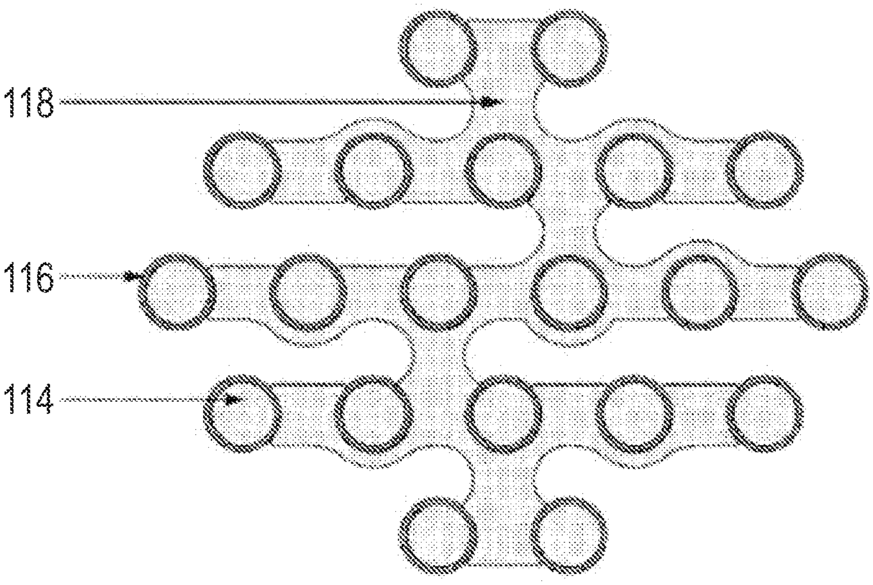
FIG. 3G is a view of the hydrogel discs and hydrogel barriers as "seen" by the patient's skin.
Figure 3H:
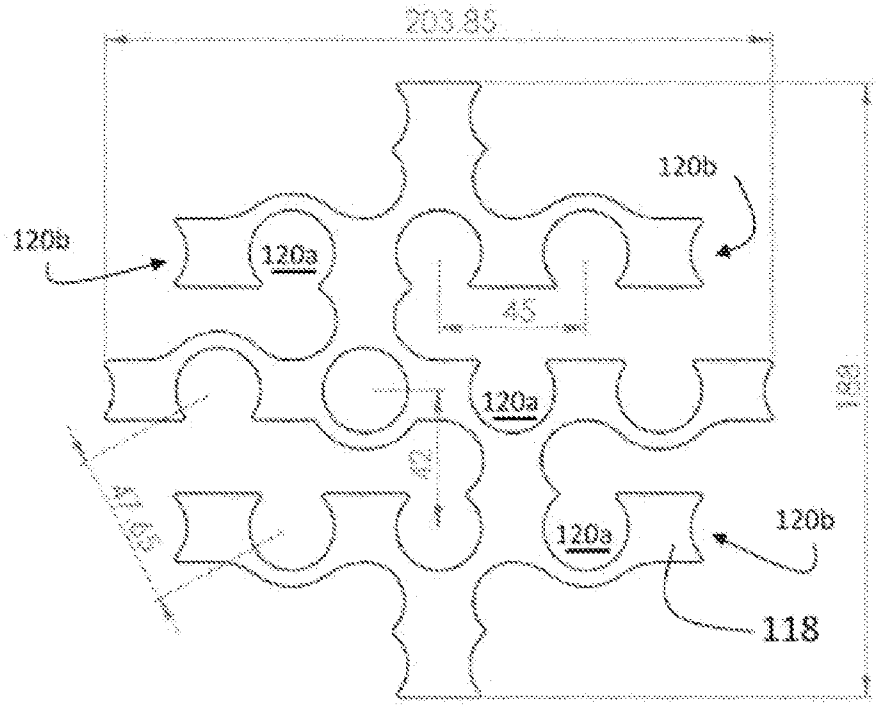
FIG. 3H is a plan view of a skin-level adhesive layer used in the transducer array illustrated in FIG. 3A.
Figure 3I:
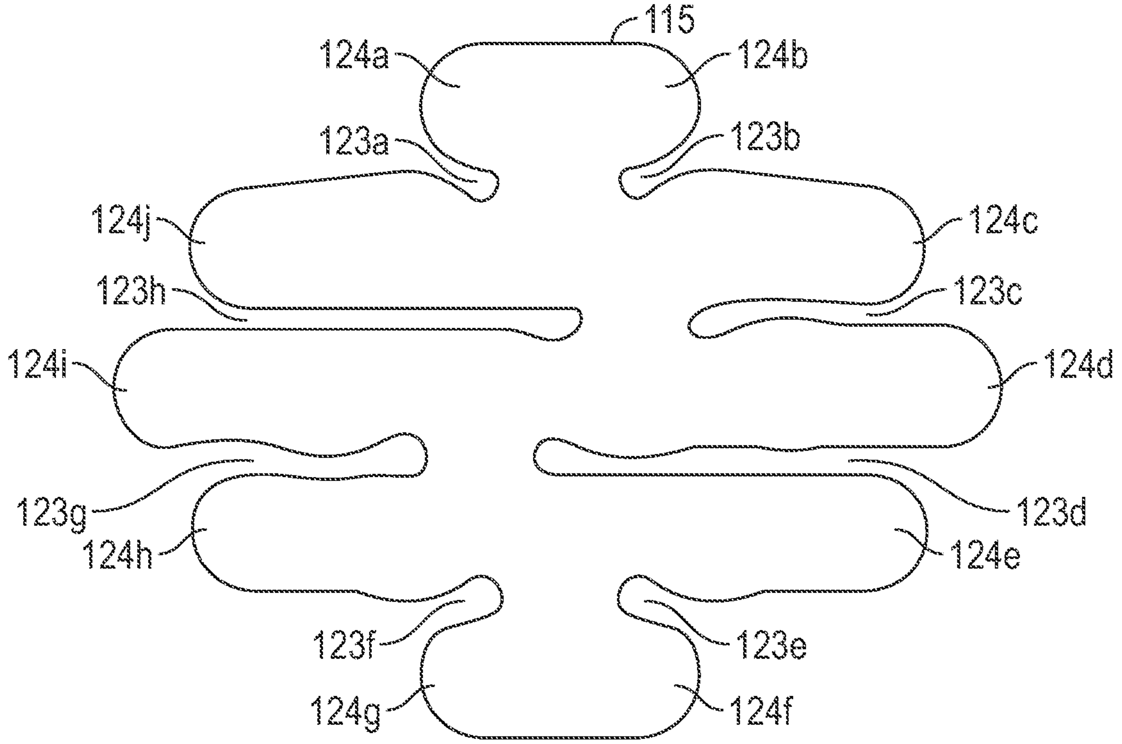
FIG. 3I is a plan view of a support layer used in the transducer array illustrated in FIG. 3A.
Figure 3J:
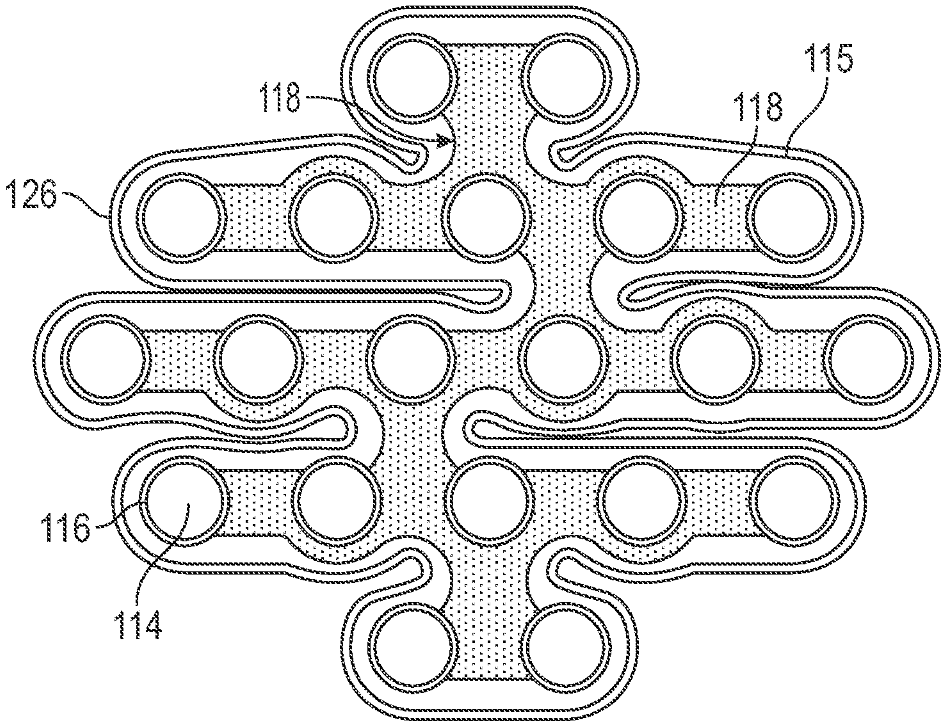
FIG. 3J is a plan view of the support layer of FIG. 3J connected to the top layer as "seen" by the patient's skin.
Figure 3K:
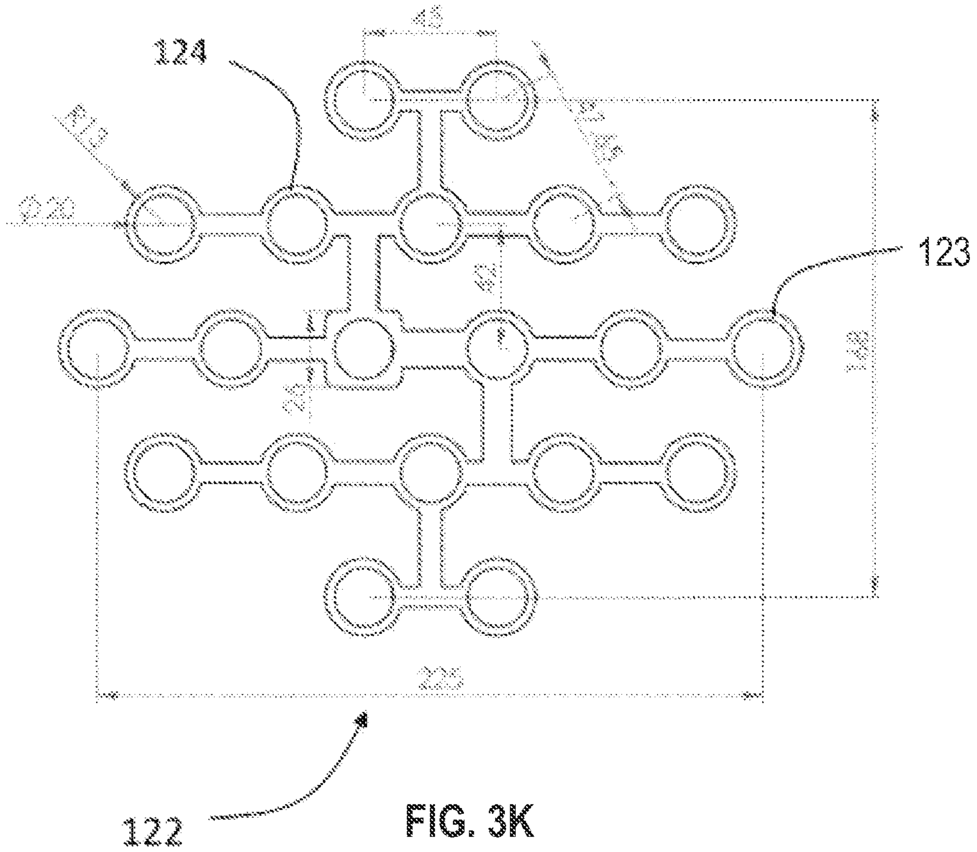
FIG. 3K is a plan view of a foam layer used in the transducer array illustrated in FIG. 3A.
Figure 3L:
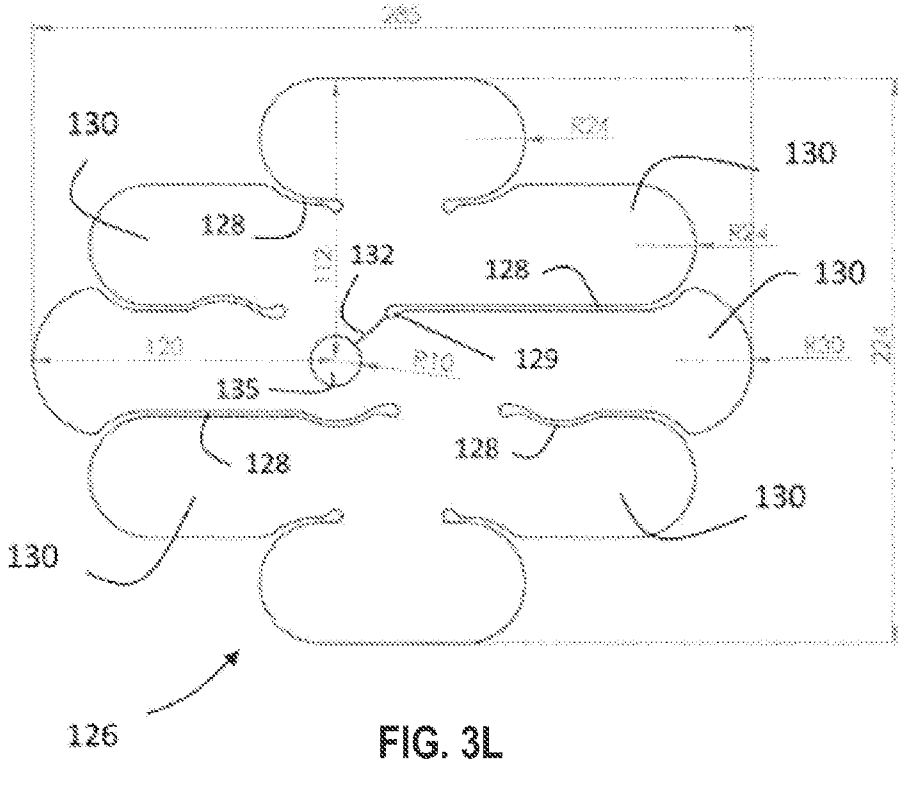
FIG. 3L is a plan view of a top, covering adhesive-backed layer used in the transducer array illustrated in FIG. 3A.
Figure 3M:
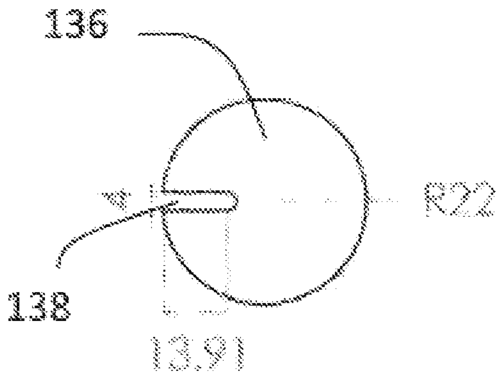
FIG. 3M is a plan view of a slot cover used in the transducer array illustrated in FIG. 3A.
Figure 3N:
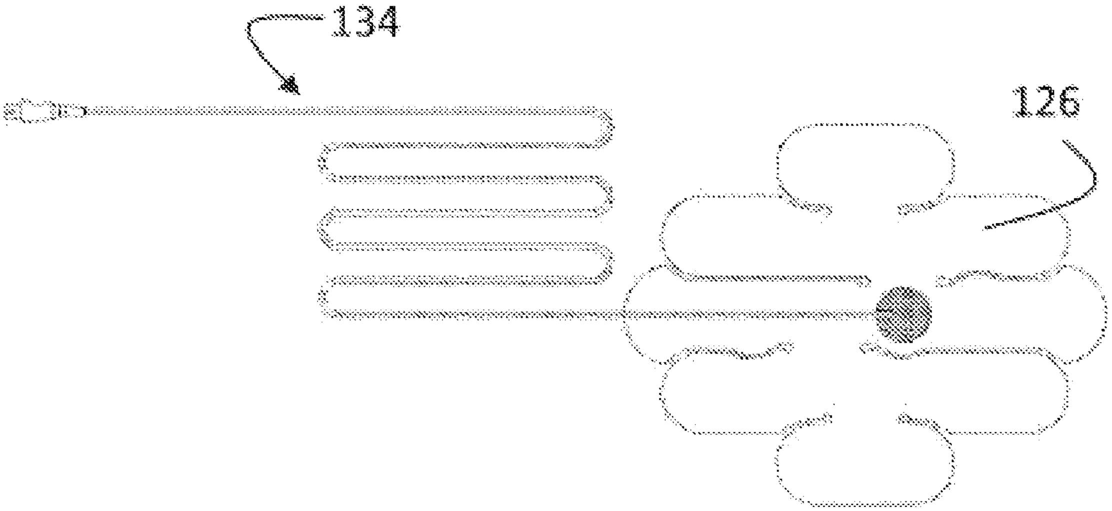
FIG. 3N is a plan view illustrating an appearance of a transducer array as illustrated in FIG. 3A as applied to a patient.
Figure 3O:
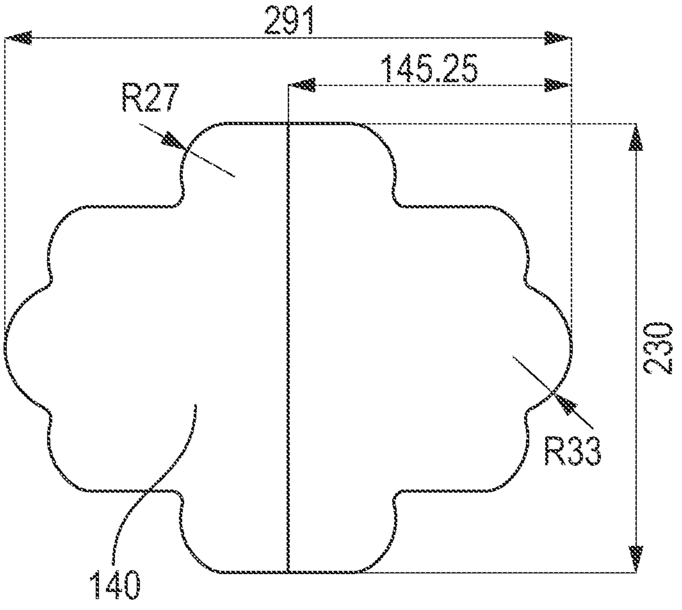
FIG. 3O is a plan view of a release liner used in the transducer array illustrated in FIG. 3A.
Figure 3P:
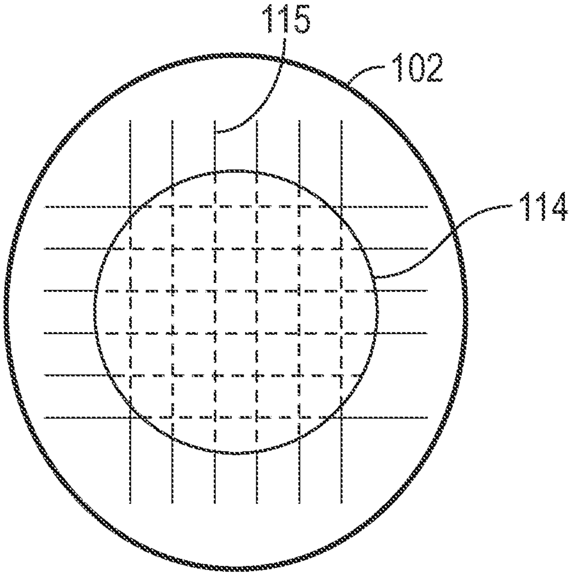
FIG. 3P is a plan view of a support layer adhered to the flex circuit with a hydrogel material.

FIGS. 3A-3P depict a first embodiment of a transducer array 100 incorporating the pads 42*a* and 42*b*. The pads 42*a* and 42*b* are referred to below as "electrode elements." The transducer array 100 is also referred to herein as an "electrode apparatus" with a first layout of electrode elements, with FIG. 3A being an exploded or assembly view showing all of the various components and their arrangement relative to each other. FIGS. 3B-3P show the individual components in greater detail.

One of the components that defines the configuration of the transducer array 100 is the flex circuit 102 (FIGS. 3A and 3B), which may be made with electrical traces extending along the branches of the flex circuit 102 as is well known in the art. The flex circuit 102 has a branching or ramified configuration. There is a central trunk 108*a*-108*g* that extends in a longitudinal direction. There are also a plurality of branches that extend laterally from both sides of the trunk 108*a*-*g* of the flex circuit 102. In some embodiments (including the embodiments depicted in FIGS. 3A, 3B, and 3K), these branches are perpendicular to the longitudinal direction and are arranged as rows 106*a*-106*e* of the flex circuit 102. In the illustrated embodiment, each of the rows 106*a*-*e* of the flex circuit 102 includes two branches—one on either side of the trunks 108*a*-108*g*. The proximal end of each branch is connected to and extends from the trunk 108*a*-*g* of the flex circuit 102, while the distal end of each branch remains free. Advantageously, this configuration improves the flexibility of the flex circuit 102, and reduces tensile stresses applied on the transducer array 100 by skin movement (bending, stretching, twisting, breathing, etc.), thereby improving and prolonging adhesion of the transducer array 100 to the skin. The transducer array 100 also improves user comfort and reduces skin damage. Note that in the embodiment illustrated in FIGS. 3A and 3B, the trunk 108*a*-108*g* shifts back and forth in segments between successive rows of the flex circuit 102. In these embodiments, only some of the segments 108*a*, 108*c*, 108*e*, and 108*g* extend in the longitudinal direction, and those longitudinal segments are interconnected by additional segments 108*b*, 108*d*, and 108*f* that extend in the lateral direction. As a result, in these embodiments, the trunks 108*b*, 108*d*, and 108*f* shift back and forth in the lateral direction as the trunks 108*a*, 108*c*, 108*e* and 108*g* extend in the longitudinal direction. In alternative embodiments, the trunk is straight.

The flex circuit 102 includes a number of mounting pads 104 arranged along the rows 106*a*-106*e*. A number of electrode elements 110 (FIGS. 3A and 3C)—for example, twenty as shown in the FIG. 3A embodiment for a typically sized adult male—are disposed on the inner (i.e., skin-facing) side of the mounting pads 104 of the flex circuit 102 (shown in FIGS. 3A and 3B) with an electrically conductive connection between each of the electrode elements 110 and the flex circuit 102. The electrode elements 110 may be on the order of 1 mm thick and 2 cm in diameter and may optionally be slightly smaller in diameter than the mounting pads 104. Each of the electrode elements 110 may be formed from a circular conductive plate that is coated with a ceramic dielectric material as is known in the art, and the circular conductor is electrically connected to an electrical contact of the flex circuit 102. The ceramic dielectric material faces toward the patient's body so that the ceramic dielectric material can make contact with the patient's skin (preferably via an intervening layer of hydrogel, as described below). The dielectric material may be a ceramic material, a non-flexible polymer, or a flexible polymer film.

The electrode elements 110 are provided with an outer side 111*a* and an inner side 111*b*. Only one of the electrode elements 110 is labeled with the reference numerals 111*a* and 111*b* for purposes of brevity. A corresponding number of stiffeners 112 (FIGS. 3A and 3D) may optionally be attached to the outer side 111*a* of the mounting pads 104 of the flex circuit 102 generally opposite the electrode elements 110 attached to the inner side 111*b*. The stiffeners 112 may be on the order of 1 mm thick and may be slightly smaller in diameter than the mounting pads 104. The stiffeners 112 may be made from any suitable material (e.g., a stiff, nonconductive plastic). In general, the stiffeners 112 help prevent the electrode elements 110 from breaking, given the flexible nature of the flex circuit 102 and the thin, fragile nature of the ceramic dielectric used for the electrode elements 110.

In some embodiments, each of the electrode elements 110 has a corresponding disc of conductive gel element 114 (FIGS. 3A, 3P, and 4) disposed on the inner side 111*b* of the electrode element 110, to establish good electrical conductivity with the patient's skin. In some embodiments, the conductive gel element 114 is slightly larger in diameter than the electrode element 110. The material is preferably gamma sterilization-compatible. For example, the conductive gel element 114 may be a hydrogel made from AG625, which is available from Axelgaard, with a thickness on the order of 635 micrometers, and with a volume resistivity of 1000 ohm-cm max. In some embodiments, the conductive gel element 114 includes one or more conductive gel layer 106 (see FIG. 4).

In some embodiments, the electrode array includes a conductive gel assembly 107, including one or more conductive gel element 114 and a support layer 115 connected to the one or more conductive gel element 114. The conductive gel element 114 includes one or more conductive gel layers 106 that may be prefabricated prior to inclusion on the electrode elements 110. In some embodiments, one or more conductive gel layers 106 may be applied in liquid form onto the electrode elements 110 and then cured (e.g., UV curing, electron beam curing) directly on the electrode element 110 and/or other portion of the transducer array 100. The support layer 115 can be applied to cover the conductive gel layer 106 and the one or more electrode elements 110, and another amount of conductive gel in liquid form or cured form may be applied to the support layer 115 so that the conductive gel layers 106 forming one of the conductive gel elements 114 are aligned and sandwich the support layer 115. In some embodiments, one or more conductive gel layers 106 may be cured directly on the support layer 115, for example and then subsequently applied to the electrode elements 110. The support layer 115 includes a first side 115*a* and a second side 115*b*. The support layer 115 is sized and dimensioned to extend over one or more electrode elements 110. The conductive gel layer 106*a* is disposed upon and attached to the first side 115*a* of the support layer 115. The conductive gel layer 106*b* is disposed upon and attached to the second side 115*b* of the support layer 115. The support layer 115 can be disposed on both of the first side 115*a* and the second side 115*b* to encapsulate a portion of the support layer 115 between the conductive gel layers 106*a* and 106*b*. The conductive gel assembly 107 can be manufactured separately from the other components of the transducer array 100 and subsequently connected to the transducer array 100. Or, the conductive gel assembly 107 can be manufactured with the transducer array 100, such as by forming the conductive gel layer(s) 106 on the electrode elements 110 either before or after application of the support layer 115 over the electrode elements 110.

The bulk electron transport agent(s) may be any substance that is capable of enhancing the electrical and/or thermal conductivity of the conductive gel. In certain non-limiting embodiments, the bulk electron transport agent(s) includes one or more ionic compounds, one or more metals, or one or more non-metals, as well as any combinations thereof. In certain non-limiting embodiments, the bulk electron transport agent comprises an amorphous carbon and/or a crystalline carbon. Particular (but non-limiting) examples of bulk electron transport agents that may be utilized in accordance with the present disclosure include carbon black, graphene, and graphite.

In some embodiments, the conductive gel element 114 and/or the one or more conductive gel layer 106 are formed primarily of a conductive gel or semi-solid conductive gel such as described below. The conductive gel element 114 may be in any form that allows the electrode elements 110 to function in accordance with the present disclosure. For example (but not by way of limitation), the conductive gel element 114 may be in the form of a hydrogel or a hydrocolloid.

The conductive gel element 114 may have properties including, but not limited to, high conductivity, tackiness, and/or biocompatible for extended periods of time. For example, the conductive gel element 84 may include AG603 Hydrogel, available from AmGel Technologies, having a principle place of business in Fallbrook, California.

The conductive gel element 114 may be used with modified hydrogels, including but not limited to perforations, recesses, and/or protrusions. Such features are further disclosed in detail in U.S. patent application Ser. No. 17/313,114, filed May 6, 2021, entitled "Conductive Gel Compositions Comprising Bulk Electron Transport Agents and Methods of Production and Use Thereof", which is hereby incorporated in its entirety.

In some embodiments, the conductive gel element 114 may be sterile. In some embodiments, the conductive gel element 114 may be configured such that the conductive gel element 114 does not substantially degrade upon exposure to sterilization conditions that include gamma rays or ethylene oxide gas, for example.

The conductive gel element 114 may be formed of any hydrophilic polymer that allows the conductive gel element 114 to function in accordance with the present disclosure. For example (but not by way of limitation), the conductive gel element 114 may be a polyacrylic acid gel, a povidone gel, or a cellulose gel. In addition, the conductive gel may comprise at least one of chitosan, alginate, agarose, methylcellulose, hyaluronan, collagen, laminin, matrigel, fibronectin, vitronectin, poly-1-lysine, proteoglycans, fibrin glue, gels made by decellularization of engineered and/or natural tissues, as well as any combinations thereof. Further, the conductive gel element 84 may comprise at least one of polyglycolic acid (PGA), polylactic acid (PLA), poly-caprolactone (PCL), polyvinyl alcohol (PVA), polyethylene glycol (PEG), methyl methacrylate, poly(methyl methacrylate) (PMMA), poly(2-hydroxyethyl methacrylate) (Poly-HEMA), poly(glycerol sebacate), polyurethanes, poly(isopropylacrylamide), poly(N-isopropylacrylamide), or any combination thereof.

In some embodiments, the conductive gel element 114 may comprise one or more of the following chemical and structural features/properties: a polymer chain length in a range of from about 1 nm to about 200 nm; a pH in a range of from about 6 to about 8; a volume resistivity of less than about 100 Ohm-in; a skin adhesion rate of at least about 100 g/inch; and a thickness in a range of from about 10 mil to about 50 mil.

In some embodiments, the conductive gel element 114 may be optimized for use at body temperature (i.e., in a range of from about 34° C. to about 40° C.) for extended periods of time.

The polymer(s) of the conductive gel element 84 may be provided with any polymer chain length that allows the conductive gel element 114 composition(s) to function as described herein. For example (but not by way of limitation), the polymer chain length may be within the range of about 1 nm, to about 200 nm, and above, as well as a range that combines any two of the values within (i.e., a range of from about 3 nm to about 175 nm, a range of from about 5 nm to about 150 nm, or a range of from about 10 nm to about 125 nm, a range of from about 15 nm to about 100 nm, etc.), and a range that combines two integers that fall between two of the above-referenced values (i.e., a range of from about 3 nm to about 157 nm, etc.).

In some embodiments, the range of the polymer chain length may be dependent upon the frequency(ies) of the alternating electric field. For example (but not by way of limitation), the range of the polymer chain length may be based upon a range of frequencies of the alternating electric field. Non-limiting examples include a range of from about 5 nm to about 50 nm when the alternating electric field has a frequency in a range of from about 50 kHz to about 150 kHz, a range of from about 50 nm to about 100 nm when the alternating electric field has a frequency in a range of from about 150 kHz to about 300 kHz, etc.

The conductive gel element 114 may be provided with any pH that does not damage the skin of a patient. For example (but not by way of limitation), the conductive gel element 84 may have a pH of about 6, about 6.5, about 7, about 7.5, about 8, as well as a range formed from any of the above values (i.e., a range of from about 6 to about 8, a range of from about 6.5 to about 7.5, etc.).

The conductive gel element 114 may be provided with any level of volume resistivity that maximizes the conductivity of the gel. For example (but not by way of limitation), the conductive gel element 114 may have a volume resistivity within a range of less than about 100 Ohm-in to less than about 10 Ohm-in, or lower, as well as a range formed of any of the above values within (i.e., a range of from about 10 Ohm-in to about 100 Ohm-in, etc.) and a range that combines two integers that fall between two of the above-referenced values (i.e., a range of from about 13 Ohm-in to about 96 Ohm-in, etc.).

The conductive gel element 114 may be provided with any skin adhesion rate that allows the conductive gel element 114 to function in accordance with the present disclosure. For example (but not by way of limitation), the skin adhesion rate of the gel may be within a range of at least about 100 g/inch to at least about 300 g/inch, or higher, as well as a range of any of the above values within (a range of from about 120 g/inch to about 300 g/inch, etc.), and a range that combines two integers that fall between two of the above-referenced values (i.e., a range of from about 115 g/inch to about 295 g/inch, etc.).

In some embodiments, the conductive gel element 114 may further include at least one additive. Any type of additive that allows the conductive gel element 114 to function in accordance with the present disclosure and that may optionally further enhance the conductivity and non-sensitizing properties of the conductive gel may be utilized in accordance with the present disclosure. Non-limiting examples of additives that may be utilized include at least one of a humectant, a preservative, an antibacterial agent, a vitamin, a moisturizer, or any combinations thereof, and the like.

The conductive gel element 114 may be provided with any concentration of one or more salts that allow gel compositions to function as described herein. The free salt concentration may be with the range of at least about 0.1 mM to about 1M, or higher, as well as any range that combines any two of the values within (e.g., range of about 0.1 mM to about 100 mM, a range of about 1 mM to about 50 mM).

The conductive gel assembly 107 may be provided with any thickness ti that allows the conductive gel element 84 to function in accordance with the present disclosure. Non-limiting examples of thicknesses $t_1$ that may be utilized in accordance with the present disclosure include a range of about 1 mil to about 100 mil, or higher, as well as a range that combines any two of the above-referenced values (i.e., a range of from about 10 mil to about 50 mil, etc.), and a range that combines two integers that fall between two of the above-referenced values (i.e., a range of from about 12 mil to about 48 mil, etc.).

In some embodiments, the conductive gel assembly 107 and the conductive gel element 114 may have a shelf life of at least about six months. For example (but not by way of limitation), the conductive gel element 114 has a shelf life of at least about 9 months or at least about 12 months.

Figure 4:
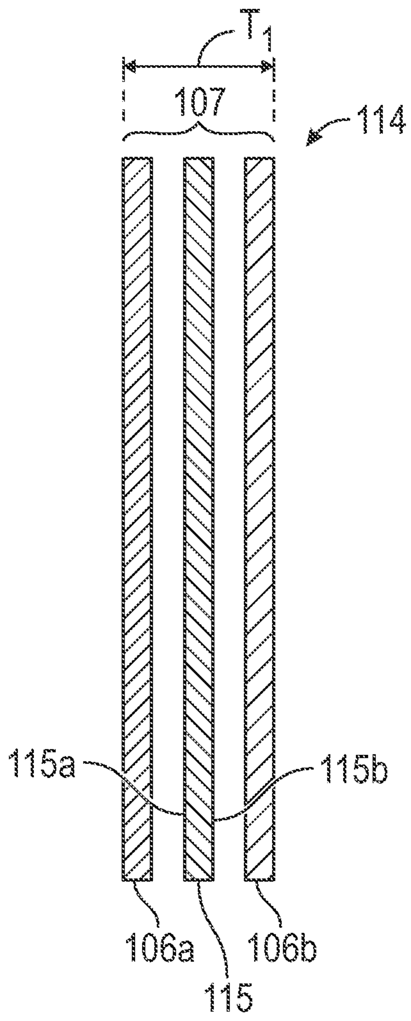
FIG. 4 is an exploded side view of a conductive gel assembly having conductive gel layers on both sides of a support layer in accordance with the present disclosure.

The one or more support layers 115 may be provided within the conductive gel element 114 (as shown in FIG. 4) or outside of the conductive element as shown in FIG. 3A. Generally, the one or more support layers 115 may be configured to provide reinforcement to the conductive gel element 114 to prevent lateral movement of the conductive gel element 114 when the conductive gel element 114 is applied to the skin of the patient. To that end, the one or more support layer 115 may provide strength and/or support to the one or more conductive layer 106 (e.g., conductive gel layers 106*a* and/or 106*b*). The one or more support layer 115 may be constructed of a woven or nonwoven material. In some embodiments, at least a portion of the one or more support layer 115 may include Reemay (i.e., spun nylon). In some embodiments, at least a portion or the entirety of the one or more support layer 115 may be constructed of a nonconductive material. In some embodiments, at least a portion or the entirety of the one or more support layer 115 may be constructed of a non-metal conductive material, such as carbon.

The support layer 115 may serve as an anchor between the conductive gel layer(s) 106 and one or more other components within the transducer array 100, such as the electrode elements 110 or the flex circuit 102 by attaching the support layer to the electrode elements 110 or the flex circuit 102, for example with a bond separate from any bond provided by the conductive gel layer(s) 106. In some embodiments, at least a portion of the support layer 115 may extend between at least two components of the transducer array 100, such as the electrode elements 110, or the conductive gel elements 114. For example, as illustrated in FIG. 3A, the support layer 115 extends between the electrode elements 110 and the conductive gel elements 114. In some embodiments, the conductive gel elements 114 may be positioned such that each conductive gel element 114 is aligned with one electrode element 110.

A gap may exist between each electrode element 110 such that each electrode element 110 is positioned at a distance from any adjacent electrode element 110. To that end, the conductive gel in liquid form or semi-solid conductive gel forming the conductive gel layer 106*a* and/or 106*b* may be dispensed onto the support layer 115 at pre-determined particular locations during formation of the transducer array 100 (e.g., corresponding to a single electrode element 110, corresponding to two electrode elements 110, corresponding to multiple electrode elements 110, and the like). In some embodiments, one or more dielectric materials may be positioned within the gap between adjacent isolated electrode elements 110, for example.

Additionally, a ring-shaped hydrogel barrier 116 (FIGS. 3A, 3F, 3G and 3J) is optionally provided, surrounding each of the conductive gel elements 114. In general, the hydrogel barriers 116 help maintain the integrity of the conductive gel elements 114 throughout the duration of wear and prevent migration of the hydrogel from its correct location under the electrode elements 110. The hydrogel barriers 116 may be made, e.g., from MED 5695R, available from Vancive Medical Technologies, which is a polyethylene foam, and may be single-coated with WetStick™ synthetic rubber adhesive, also available from Vancive Medical Technologies. The hydrogel barriers 116 may be 500 micrometers thick, and are preferably gamma sterilization-compatible.

To increase patient comfort, the transducer array 100 may optionally include a conformal foam layer 122 (FIGS. 3A and 3K) positioned beneath the flex circuit 102, and shaped to closely follow the branching configuration of the flex circuit 102. Note that unlike the flex circuit 102 (which has solid circular mounting pads 104 for the electrode elements 110), the foam layer 122 has ring-shaped regions 123 that surround the electrode elements 110 so as not to intervene between the electrode elements 110 and the patient's skin. A suitable thickness for the conformal foam layer 122 is on the order of 1 mm, and the foam layer 122 is preferably the same thickness as the electrode elements 110. The foam layer 122 preferably covers the entire surface of the flexible flex circuit 102 (except for the regions where the electrode elements 110 are positioned) while maintaining overall flexibility and conformability of the transducer array 100. But in alternative embodiments, the foam layer 122 only covers a portion of the surface of the flexible flex circuit 102. In some embodiments, the size of the foam layer 122 may be minimized to the extent possible so as not to reduce the overall breathability and fluid-vaporizing properties of the transducer array 100.

The conformal foam layer 122 may be made, e.g., from polyethylene foam such as MED 5696R available from Vancive Medical Technologies. The conformal foam layer 122 may be affixed to the flex circuit 102 using a suitable adhesive (e.g., WetStick™ synthetic rubber adhesive, also available from Vancive Medical Technologies). The foam layer 122 advantageously protects the patient from potentially sharp edges of the conductive traces on the flex circuit 102. This is particularly important in the context of flexible transducer arrays because flexing the transducer arrays 100 can cause the flat conductive traces to twist, which can cause the potentially sharp edges of those conductive traces to tilt down towards the patient's skin. Notably, interposing the foam layer 122 between the conductive traces of the flex circuit 102 and the patient's skin protects the patient from cuts and/or pain that might be caused by those potentially sharp edges.

The transducer array 100 also includes a skin-level layer of adhesive 118*a* disposed beneath the foam layer 122, as shown in FIGS. 3A, 3H, and 3J. (The skin-level adhesive 118*a* also appears in FIG. 3G.) In general, the skin-level layer of adhesive 118*a* follows the branching configuration of the flex circuit 102 and the foam layer 122, but with the various branches and trunk portions of the skin-level adhesive 118*a* being slightly wider than the corresponding portions of the flex circuit 102 and the foam layer 122 so as to at least partially overlap with the spaces between the branches of the flex circuit 102 and the foam layer 122. Notably, the skin-level adhesive 118*a* includes cutouts 120*a* along the branches of the adhesive, and cutouts 120*b* at the free ends of the branches of the adhesive. These cutouts 120*a*, 120*b* are shaped so as not to intervene between the electrode elements 110 or the conductive gel elements 114 and the patient's skin. The skin-level layer of adhesive 118*a* also functions as a constructive element, to stabilize the central area around the electrode elements 110 to prevent movement of the electrode elements 110 relative to the patient's skin.

The skin-level layer of adhesive 118*a* may be made from a polyester/rayon-blend, spunlace non-woven tape material such as 3M® 9917, which is 30 micrometers thick. The tape may be double-coated with acrylate adhesive, to provide a peel strength on the skin-facing side (e.g., 23 lbf/inch) and a higher peel strength (e.g., 27 lbf/inch) on the opposite, outer side. The material is preferably hypoallergenic, highly conformable, and breathable; with a high moisture vapor transmission rate; and it is preferably gamma sterilization-compatible. To prevent excessive sweating and moisture from being trapped under the transducer array 100, the overall surface area of the skin-level layer of adhesive 118*a* may be minimized, e.g., by making it just slightly wider than the corresponding portions of the flex circuit 102 and the foam layer 122.

Note that in embodiments where a conformal foam layer 122 is omitted, the layer of adhesive 118*a* may be connected directly to the flex circuit 102 with no intervening components disposed therebetween. Alternatively, in those embodiments where the conformal foam layer 122 is provided, the layer of adhesive 118 may be connected indirectly to the flex circuit 102, with a foam layer 122 disposed therebetween. In these embodiments, the foam layer 122 may be connected to the flex circuit 102 with a bonding material, such as an adhesive or a cohesive.

An exemplary embodiment of the support layer 115 is shown in FIGS. 3I and 3J. The support layer 115 (FIGS. 3A, 3I, and 3L) is positioned below and connected to an inner side of the flex circuit 102, the inner side 111*b* of the electrode elements 110 or combinations thereof. The support layer 115 has a number of slots 123, which divide the support layer 115 into a number of separate fingers 124, each of which is underneath a respective branch of the flex circuit 102. The support layer 115 is provided with 8 slots 123*a-h*, and 10 fingers 124*a-j*. The slots 123*a-h* are preferably significantly narrower than the fingers 124*a-j* and the fingers 124*a-j* are preferably wider than the diameters of the electrode elements 110. This configuration results in the fingers 124*a-j* of the support layer 115 overlapping with the spaces between the branches of the flex circuit 102. The transducer array 100 may also be provided with an adhesive layer 118*b* positioned between the support layer 115 and the flex circuit 102 to anchor the support layer 115 to the flex circuit 102. The fingers 124*a-j* overlie and extend between the conductive gel elements 114. The fingers 124*a-j* are connected to the conductive gel elements 114 and serve to provide lateral support for the conductive gel elements 114 so as to prevent the conductive gel elements 114 from moving laterally when the conductive gel elements 114 are applied to the skin of the patient. The flexible nature of the support layer 115 allow the fingers 124*a-j* to move independently of each other as the branches of the flex circuit 102 move independently of each other. This, in turn, helps to maintain conformability of the transducer array 100 and adhesion to the patient's skin even as the patient moves.

A top, covering adhesive-backed layer 126 (FIGS. 3A, 3L, and 3N) is positioned above and connected to an outer side of the flex circuit 102. The covering adhesive-backed layer 126 has a number of slots 128, which divide the covering adhesive-backed layer 126 into a number of separate fingers 130, each of which overlies a respective branch of the flex circuit 102. The slots 128 are preferably significantly narrower than the fingers 130 and the fingers 130 may be wider than the diameters of the electrode elements 110. This configuration results in the fingers 130 of the covering adhesive-backed layer 126 overlapping with the spaces between the branches of the flex circuit 102 to provide maximal adhesion of the covering adhesive-backed layer 126 to the patient's skin around the electrode elements, while still allowing the fingers 130 of the covering adhesive layer to move independently of each other as the branches of the flex circuit 102 move independently of each other. This, in turn, helps to maintain conformability of the transducer array 100 and adhesion to the patient's skin even as the patient moves. In addition, the covering adhesive-backed layer 126 preferably extends beyond the perimeter of the flex circuit 102 to provide additional adhesion to the skin at the outer boundary of the transducer array 100.

The covering adhesive-backed layer 126 may be made from 3M® 9916, which is a 100% polyester, spunlace non-woven tape, for example. This material may be single-coated with acrylate adhesive on the skin-facing side, which adheres the covering adhesive-backed layer 126 to the outer surface of the flex circuit 102. The material forming the covering adhesive-backed layer 126 may have a thickness of 40 micrometers. The covering adhesive-backed layer 126 may be hypoallergenic, highly conformable, breathable, and/or gamma sterilization-compatible.

As shown in FIG. 3J, the support layer 115 may be shaped to be within the confines of the layer 126. Further, the support layer 115 may be shaped so that the fingers 124 of the support layer underlie and are aligned with fingers 130 of the layer 126 so that the fingers 124 move with the fingers 130.

Shown in FIG. 3P is a bottom plan view of a portion of the transducer assembly 100 depicting the support layer 115 adhered to the flex circuit 102, and positioned between the conductive gel element 114 and the flex circuit 102. In some embodiments, the transducer array 100 can be made by attaching the support layer 115 to the flex circuit 102 such that the electrode elements 110 are between the support layer 115 and the flex circuit 102. In this position, the conductive gel elements 114 can be applied in liquid form to the support layer 115 directly over the electrode elements 110 and then cured. In this embodiment, at least some of the liquid forming the conductive gel elements 114 may pass through the support layer 115 thereby forming the layers 106*a* and 106*b* encapsulating the support layer 115 in the conductive gel elements 114 when cured. Further, the conductive gel elements 114, when cured, may adhere to the electrode elements 110 thereby providing further lateral support to the conductive gel elements 114 separate from the adhesive layer 118*b* attaching the support layer 115 to the flex circuit 102. In some embodiments, the support layer 115 can be anchored to the flex circuit 102 in a manner other than an adhesive. For example, a mechanical linkage such as thread, staple or rivet can be used to connect the support layer 115 to the flex circuit 102.

Notably and advantageously, two separate factors contribute to the adhesion of the entire transducer array 100 to the patient's skin. The first factor is the portions of the lower surface of the top adhesive layer 126 that contact the skin through the spaces between the branches of the flex circuit 102 and beyond the perimeter of the flex circuit 102. The second factor is the layer of adhesive 118*a* disposed between the foam layer 122 and the person's skin (or, between the flex circuit 102 and the person's skin in those embodiments that do not include the foam layer 122). The inclusion of these two separate adhesive components provides significantly improve adhesion of the transducer array 100 to the patient's skin. This feature of the transducer array 100 enhances the degree of adhesion of the transducer array 100 to the patient's skin around the electrode elements, resulting in prolonged and better skin/electrode contact as compared to configurations in which the only adhesion was provided by an adhesive-backed patch overlying the entire transducer array.

In some embodiments, the covering adhesive-backed layer 126 includes a central aperture 135 and a slit 132 extending from the innermost end 129 of one of the slots 128—in particular, the innermost slit-end that is closest to the central aperture 135. The central aperture 135 permits an electrical cable 134 (shown in FIG. 3N) that protrudes from the back surface of the flex circuit 102 to extend through the covering adhesive-backed layer 126. This electrical cable 134 is used to connect the flex circuit 102 to a TTFields therapy controller (not illustrated) via a connector. The slit 132 is useful for positioning the adhesive-backed layer 126 over the flex circuit 102 after the cable 134 has been connected to the flex circuit 102 during the assembly process. In particular, portions of the covering adhesive-backed layer 126 can be moved away from each other to open the slit 132, such that the covering adhesive-backed layer 126 can be passed around the electrical cable 134 on either side and then the entire adhesive-backed layer can be pressed into proper position.

Once the transducer array 100 has been properly attached to the patient's skin with the covering adhesive-backed layer 126 securing the transducer array 100 in place, the central aperture 135 may be covered, for protection, with a top adhesive-backed slot-cover 136 (FIGS. 3A, 3M, and 3N). The slot-cover 136 may be a disc-shaped item, formed from the same material and in the same manner as the covering adhesive-backed layer 126. In some preferred embodiments, the slot cover 136 includes a slot 138 for the electric cable 134 to pass through.

In some embodiments, the entire assembly of components described above is protected, prior to use on a patient, with a two-part release liner 140 (FIGS. 3A and 30). The release liner 140 has an overall shape that generally follows, but may be slightly larger than, the outer periphery of the covering adhesive-backed layer 126. It may be made from, for example, AR W4000, available from Adhesive Research, which is a white, silicone-coated PET (polyethylene terephthalate) material that is 50 micrometers thick.

In the FIGS. 3A-3O embodiment of a transducer array 100 described above, there are 20 electrode elements arranged in five rows, with two, five, six, five, and two electrode elements in each of the successive rows. (The rows correspond with the branches of the flex circuit 102 and are perpendicular to the longitudinal direction in which the trunk 108 extends. Thus, the rows are oriented horizontally and the trunk 108 is oriented vertically as the transducer array 100 is oriented in FIG. 1 and the flex circuit 102 is oriented in FIG. 2.) Depending on factors such as the size, sex, age, etc. of a patient, however, there could be more or less electrode elements 110 arranged in different configurations, while still adhering to the inventive concepts disclosed herein.

In both the FIGS. 3A-3P embodiment, the flex circuit 102 has a plurality of branches extending on each lateral side of the trunk region. But in alternative embodiments, the branches may be present only on a single lateral side of the trunk region (in which case, the trunk region would be located near one edge of the apparatus.

In some embodiments (including but not limited to the FIGS. 3A-3P embodiment) the flex circuit 102 is configured so that no more than three paths emanate from any given intersection on the flex circuit 102. For example, in FIG. 3B, one path of the flex circuit 102 emanates from the intersections at the mounting pads 104*a,* two paths of the flex circuit 102 emanate from the intersections at the mounting pads 104*b*, and three paths of the flex circuit emanate from the intersections at the mounting pads 104*c*. Notably, there are no intersections on the flex circuit 102 from which more than three paths emanate. This holds true for both the intersections that are positioned at the mounting pads 104, and also for intersections that are not positioned at one of the mounting pads 104 (e.g., The T-shaped intersections 105).

In some embodiments, including the FIGS. 3A-3P embodiments, all segments of the flex circuit 102 are straight.

In some embodiments, including the FIGS. 3A-3P embodiments, an electrical cable terminates on the flex circuit 102 (as best seen in FIG. 3N). Optionally, in these embodiments, (as best seen in FIG. 3B) segments of the flex circuit 102 near the distal end of each branch are thinner than at least some of the segments of the flex circuit 102 that are adjacent to the location where the electrical cable terminates (e.g., segment 108*d*). This configuration increases the flexibility of the flex circuit, which also contributes to improving the flexibility of the entire apparatus.

Figures 5A, 5B:
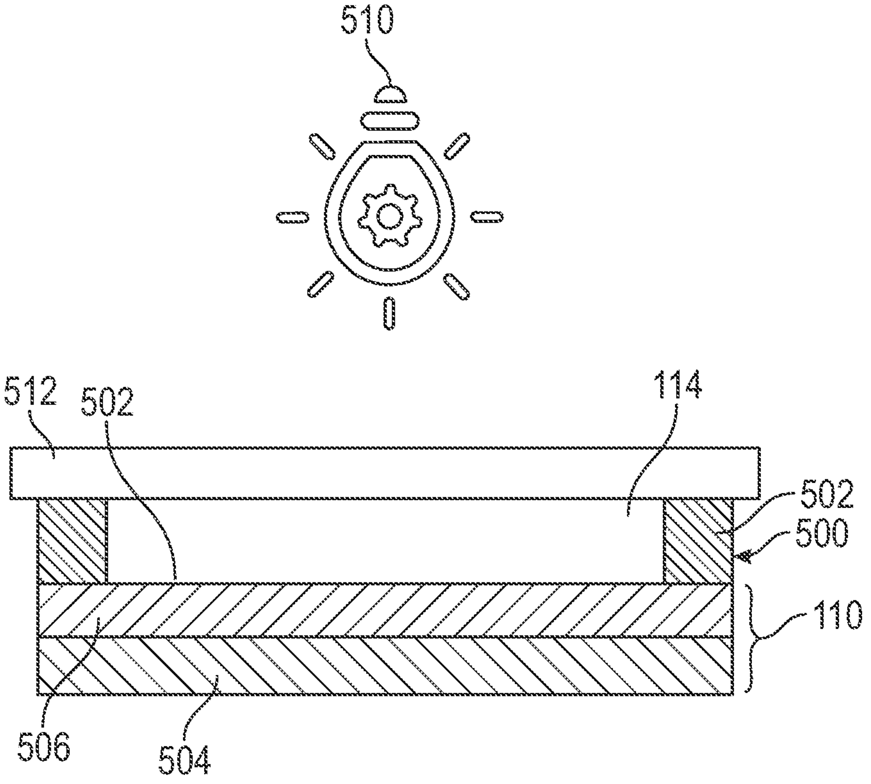
FIG. 5A is a flow chart of an exemplary method of forming conductive get layers in accordance with the present disclosure.
FIG. 5B is a partial schematic view of an exemplary transducer array constructed in accordance with the present disclosure.

FIG. 5A illustrates a flow chart 200 of an exemplary method of forming the exemplary conductive gel elements 114 in accordance with the present disclosure. In a step 204, the support layer 115 may be positioned on and optionally anchored to the electrode elements 110 and the flex circuit 102. In a step 206, conductive gel (in liquid form) or semi-solid conductive gel may be dispensed in a predetermined pattern on at least a portion of the support layer 115 and cured (e.g., UV curing, electron beam curing) to form the conductive gel elements 114. In forming the conductive gel elements 114, the conductive gel or semi-solid conductive gel may be dispensed at one or more pre-determined targeted locations onto the electrode elements 110. The electrode elements 110 may be provided in a predetermined pattern, and have a predetermined size. In these embodiments, the pre-determined targeted locations where conductive gel will be dispensed may correspond to the predetermined pattern and predetermined size of the electrode elements 110 so that when the conductive gel elements 114 are installed on the electrode elements 110, the conductive gel elements 114 each correspond to at least one electrode element 110.

In some embodiments, a mold and/or spacer may be used to provide for dispensing of the conductive gel (in liquid form) or semi-solid conductive gel at the one or more pre-determined targeted locations. For example, FIG. 5B illustrates an exemplary mold 500 disposed on a surface 502 of the electrode element 110. The electrode element 110 includes a conductive material layer 504 and a polymer layer 506. Generally, the mold 500 may be positioned prior to applying conductive gel element 114 (in liquid form) thereto. A sidewall 508 of the mold 500 may extend beyond the electrode element 110 and define a thickness for the semi-solid conductive gel element 114. Alternatively, the mold 500 may be sized and shaped to accept both the electrode element 110 and the conductive gel element 114. In this example, the electrode element 110 may be first disposed within the mold 500, with the mold 500 having a sidewall height greater than height of the electrode element 110, such that a portion of the sidewall 508 of the mold 500 that extends beyond the electrode element 110 defines a thickness for the semi-solid conductive gel element 114 produced thereon. The conductive gel element 114 may be then cured via a radiation source 510 (e.g., UV curing) such that the mold 500 provides boundaries and wall height equal to a pre-determined thickness desired for the conductive gel element 114. The curing provides the polymerized conductive gel element 114. In some embodiments, the conductive gel elements 114 may have a surface area that overlaps about 75% to 100% of the surface area of the particular electrode element 110. In some embodiments, the conductive gel elements 114 may have a surface area that overlaps about 50% to 100% of the surface area of the particular electrode element 110.

Figure 5C:
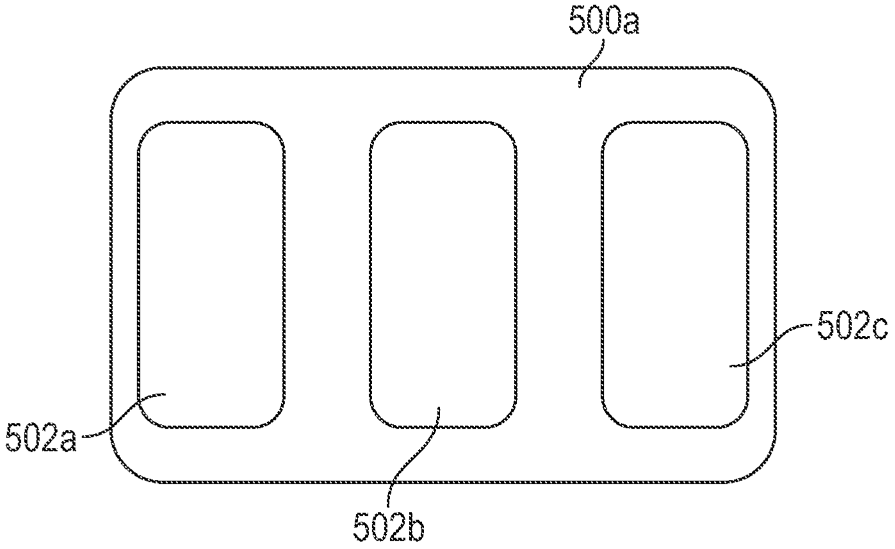
FIG. 5C is top plan view of use of a mold for in-line processing of multiple electrode elements.

Curing the conductive gel element 114 directly on the electrode element 110 allows for in-line processing. FIG. 5C depicts in-line processing of multiple elements 110 or arrays 100 using a mold 500*a* that contacts first surfaces 502*a*, 502*b* and 502*c* of three separate electrode elements 110. It should be noted that production for any number of elements 110 or arrays in batch or continuous format is contemplated.

In some embodiments, a quartz plate 512 (see FIG. 5B) may optionally be used during curing. The quartz plate 512 may be disposed on the liquid or semi-solid conductive gel element 114 applied to the surface 502 of the electrode element 110 prior to curing. The quartz plate 512 may be retained on the conductive gel element 114 during a portion or all of the curing step. The optional use of the quartz plate 512 may transfer radiation (e.g., UV light) therethrough providing homogeneous thickness of the polymerized conductive gel element 114.

Figure 5D:
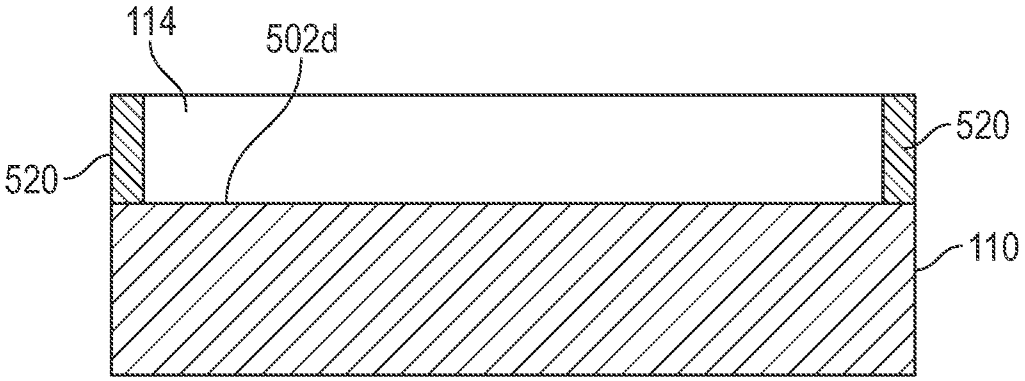
FIG. 5D is a partial schematic view of another exemplary transducer array constructed in accordance with the present disclosure.

Referring to FIG. 5D, in some embodiments, one or more barriers 520 may be applied to the surface 502*d* of the electrode element 110 to maintain the conductive gel element 114 on the electrode element 110. The barrier 520 may be formed of any material configured to be attached to the surface 502*d* of the electrode element 110 and maintain a perimeter sidewall and receiving space for the conductive gel element 114. When the barrier 520 is formed of a polymer or other porous material (such as, but not limited to, MED 5695R, available from Vancive Medical Technologies, a polyethylene foam), the conductive gel element 114 may penetrate into the barrier 520 prior to curing and increase adhesion between the conductive gel element 114 and the electrode element 110. Further, when the barrier 520 is formed of a polymer, the conductive gel element 114 may crosslink to the polymer of the barrier 520 during curing and yet further increase the adhesion between the conductive gel element 114 and the electrode element 110. Barriers 520 may be similar to hydrogel barriers 116 shown in FIGS. 3A, 3F, 3G and 3J.

The barrier 520 can be utilized with electrodes of any structure/configuration and produced from any material(s) as described herein. The use of hydrogel barriers can be particularly advantageous when a ceramic electrode is utilized (or when at least the surface on which the liquid hydrogel is disposed is formed of a ceramic material), as the hydrogel cannot crosslink to the ceramic; in this embodiment, the hydrogel barrier serves as to anchor the hydrogel to the electrode and prevent migration of the hydrogel from its correct location on the electrode.

In some embodiments, the electric field generator 32, connected to the transducer array 100, may supply a first electric signal having a first power and a first frequency to a first group of one or more electrode elements 110 at a first instance in time to generate a first TTField. The electric field generator 32, at a second instance in time, may supply a second electric signal having a second power, the same as or different from the first power, and a second frequency, the same as or different from the first frequency, to a second group of electrode elements 110 to generate a second TTField. The first TTField and the second TTField may target the same target area or may target different target areas. In one embodiment, the first instance in time and the second instance in time may overlap, that is, the electric field generator 32 may supply the second electric signal to the second group while also supplying the first electric signal to the first group. In such an embodiment, the first group and the second group may be mutually exclusive.

In some embodiments, the electric field generator 32, connected to the transducer array 100, may supply a first electrical signal having a first power and a first frequency to a first group of one or more electrode element 110 and supply a second electrical signal having a second power and a second frequency to a second group of electrode elements 110 at the same instance in time. That is, the electric field generator 32 may simultaneously supply the first electric signal to the first group and the second electric signal to the second group. While the above embodiments describe only the first group and the second group, it is understood that there may be more than two groups. In one embodiment, the number of groups is dependent on the number of combinations of the conductive regions 56*a-h*.

Referring again to FIG. 2, in some embodiments, leads 34*a* and 34*b* may include a DC blocking component, such as blocking capacitors 160*a* and 160*b*. Blocking capacitors may be operable to block DC current from passing to the pads 42*a* and 42*b*. The blocking capacitors 160*a* and 160*b* pass AC voltage to the pads 42*a* and 42*b*, and may be operable to prevent DC voltage or DC offset generated by the electric field generator 32 or otherwise present in the electrical signal from passing to or through the patient. In some embodiments, the blocking capacitors 160*a* and 160*b* may be non-polarized capacitors. In some embodiments, the blocking capacitors 160*a* and 160*b* may have a capacitance of about 1 μF. In some embodiments, the blocking capacitor is a "Goldmax, 300 Series, Conformally Coated, X7R Dielectric, 25-250 VDC (Commercial Grade)" leaded non-polarized ceramic capacitor by KEMET Electronics Corporation (Fort Lauderdale, FL).

In some embodiments, the blocking capacitors 160*a* and 160*b* may be a component of the leads 34*a* and 34*b*, or an additional component at any position between the electrode element 82 of the first pad 42*a* and second pad 42*b* and the electric field generator 32. For example, the blocking capacitors 160*a* and 160*b* may be intermediate the first end 36*a* of the second conductive lead 34*b* and the electric field generator 32, or intermediate the second end 40*b* of the second conductive lead 34*b* and the second pad 42*b*. In some embodiments, one or more blocking capacitor 160*a* and 160*b* may be provided remote from the pads 42*a* and 42*b*. For example, one or more blocking capacitors 160*a* and 160*b* may be located on a non-patient side of the electrode element 82

Certain non-limiting embodiments of the present disclosure are related to kits that include components of the TTField generating systems, such as the electronic apparatus 30, described herein. In some embodiments, one or more of the pad 42*a* and 42*b*, or transducer array 100 may be packaged as part of a kit. In some embodiments, the kit may include the first pad 42*a* and the lead 34*a* connected to the electrode elements 110. In some embodiments, the kit may include the first pad(s) 42*a* and second pad(s) 42*b*, the transducer array 100 and the leads 34*a* and 34*b*. In some embodiments, the lead 34*a* may be mechanically coupled to the first pad 42*a*, and the second conductive lead 34*b* may be mechanically coupled to the second pad 42*b*, for example, by a rivet, by solder, by adhesive, by welding, and/or other electrically conductive coupling means. In some embodiments, the kit may further include the blocking capacitor(s) 160*a* or 160*b* positioned such that the electric signal passes through the blocking capacitor 160*a* or 160*b*.

Figure 6:
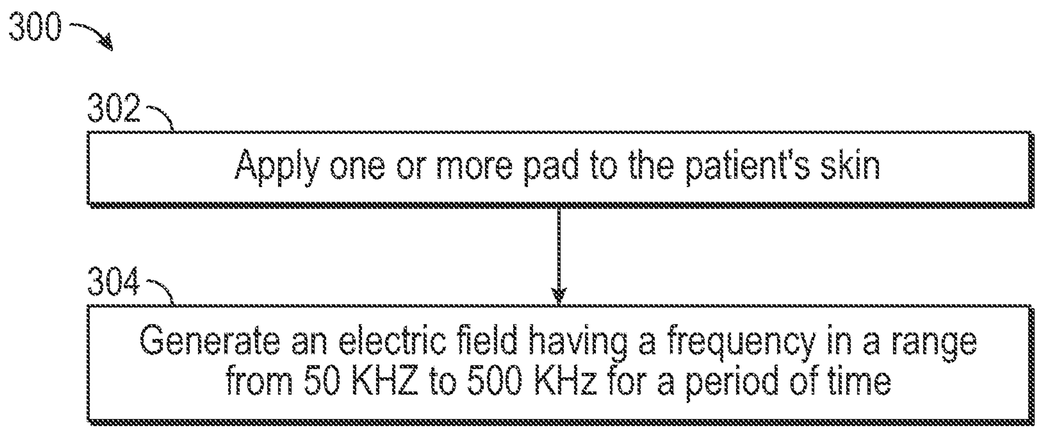
FIG. 6 is a flow chart of an exemplary method of using an electronic apparatus in accordance with the present disclosure.

Referring now to FIG. 6, shown therein is a flow chart 300 of an exemplary method of using the electronic apparatus 30 and the transducer array 100 to apply a TTField to a patient. In a step 302, the transducer array 100 may be attached to the skin of a patient. For example, electrode elements 110 may be attached to the skin of the patient on opposite sides of a tumor. In the context of a brain tumor, electrodes 110 may be positioned in the center of a person's head. For example, one of the electrode elements 110 may be positioned on the right side of the person's head, and another one of the electrode elements 110 may be positioned on the left side of the person's head. One or more electrode elements 110 may be applied to the patient's skin by a user.

In a step 304, an AC voltage is applied between the electrode elements 110. For example, the electric field generator 32 provides an alternating electric field having a frequency in a range of from about 50 kHz to about 1 MHz for a period of time to the electrode elements 110 applied to the patient to deliver TTF fields to the patient. In some embodiments, a user may initiate generation of the electric field generator 32 via the control box 28. In some embodiments, application of the AC voltage may be performed more than one time in the period of time. Duration of multiple instances of application of AC voltage may be similar or different. In some embodiments, a time period of non-application of AC voltage may be between application of AC voltage.

Figure 7A:
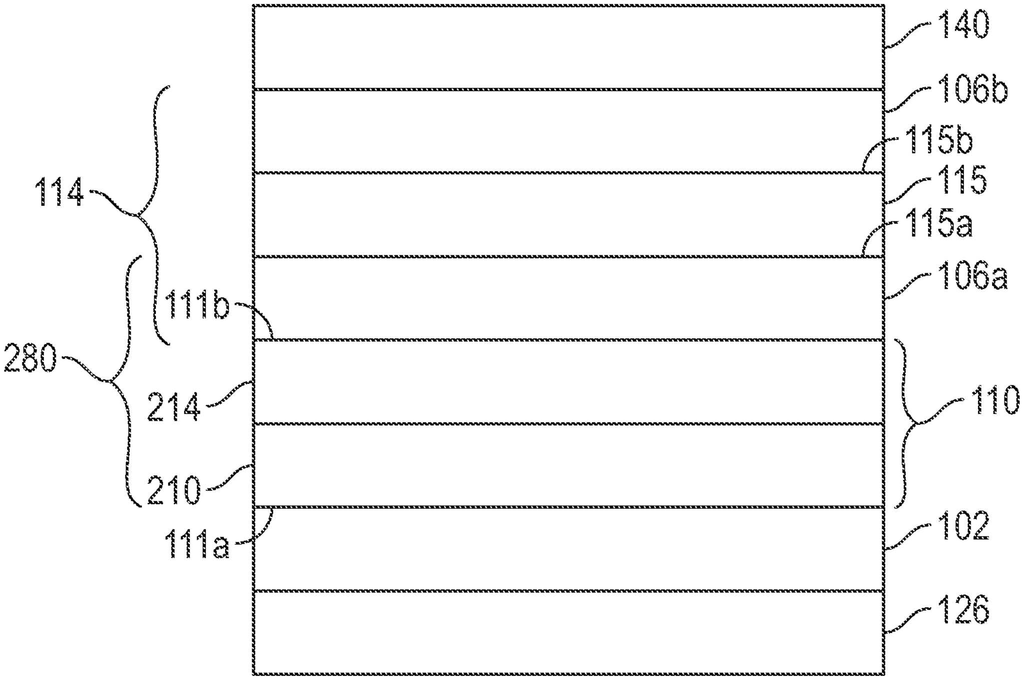
FIG. 7A is a partial schematic view of another exemplary transducer array constructed in accordance with the present disclosure.

FIG. 7A is a partial schematic view of the transducer array 100 constructed in accordance with the present disclosure. FIG. 7A is a cross-sectional view taken across one of the electrode elements 110. The electrode element 110 includes a conductive plate 210 and a dielectric material 214 positioned adjacent to and covering the conductive plate 210. The conductive plate 210 is constructed of a conductive material, such as copper, aluminum or the like. The dielectric material 214 is constructed of a non-conductive material, such as a ceramic material, a polymer material or the like.

The transducer array 100 also includes a plurality of isolated conductive gel elements 114, one of which is shown by way of example in FIG. 7A. The isolated conductive gel element 114 is in contact with the electrode element 110. The dielectric material 214 is positioned between the isolated conductive gel element 114, and serves to capacitively couple the conductive plate 210, and the isolated conductive gel element 114. The isolated conductive gel element 114 includes the first conductive gel layer 106*a* and the second conductive gel layer 106*b*. The support layer 115 is optional, and when present may be positioned in between the first conductive gel layer 106*a* in the second conductive gel layer 106*b*. As shown in FIG. 7A, the first conductive gel layer 106*a* overlaps the second conductive gel layer 106*b*. As will be explained in more detail below, the first conductive gel layer 106*a* may be applied to the plurality of electrode elements 110 in a flowable state, and then cured on the electrode elements 110. The first side 115*a* of the support layer 115 may be applied onto the first conductive gel layer 106*a*, and the second conductive gel layer 106*b*, in a flowable state, may be applied onto the second side 115*b* of the support layer 115 such that the first and second conductive gel layers 106*a* and 106*b* on each of the electrode elements 110 overlap. Once the second conductive gel layer 106*b* is applied, the second conductive gel layer 106*b* may be cured on the second side 115*b* of the support layer 115. As discussed above, the support layer 115 may be provided with a plurality of pores which permit the second conductive gel layer 106*b* to flow through the pores and engage the first conductive gel layer 106*a* prior to curing the second conductive gel layer 106*b*.

The release liner 140 is in contact with and covers the second conductive gel layer 106*b*. The release liner 140 may be applied to the second conductive gel layer 106*b* subsequent to curing the second conductive gel layer 106*b*.

The first conductive gel layer 106*a* may have a thickness of within a range of approximately 0.1 mm to approximately 4 mm and combinations therein (e.g, a range of from 0.1 mm to about 1.4 mm, a range of from about 0.2 mm to about 3 mm, etc.). The second conductive gel layer 106*b* may have a thickness within a range of approximately 0.1 mm to approximately 4 mm and combinations therein (e.g., a range of from 0.1 mm to about 1.4 mm, a range of from about 0.2 mm to about 3 mm, etc.).

Any dielectric polymer material(s) known in the art or otherwise contemplated herein may be present in the electrodes utilized in accordance with the present disclosure. Non-limiting examples of polymers that may be utilized to form the electrode (and in particular, to form a polymer layer of an electrode) include PVDF, poly(vinylidene fluoride-trifluoroethylene-chlorotrifluoroethylene), and/or poly(vinylidene fluoride-trifluoroethylene-1-chlorofluoroethylene). Those two polymers are abbreviated herein as "Poly(VDF-TrFE-CtFE)" and "Poly(VDF-TrFE-CFE)," respectively. These polymers have a high dielectric constant (i.e., on the order of 40). Alternatively, other polymer(s) that provides a high level of capacitance (i.e., a dielectric constant of at least 20 at least one frequency between 100 kHz and 500 kHz) may be used.

In addition, in certain non-limiting embodiments, ceramic nanoparticles may be mixed into the polymer to form a "nanocomposite." Optionally, these ceramic nanoparticles may comprise ferroelectric metal oxides (e.g., at least one of barium titanate and barium strontium titanate).

When the electrode element 110 comprises a conductive material layer and a flexible polymer layer, the layer of conductive material may comprise at least one metal (such as, but not limited to, stainless steel, gold, and/or copper).

When the dielectric material 214 is constructed of a ceramic material, the ceramic material may be porous. When the first conductive gel layer 106*a* is applied to the dielectric material 214, a portion of the first conductive gel layer 106*a* in the flowable state may flow into the pores and thereby penetrate the dielectric material prior to curing the first conductive gel layer 106*a*. Once cured, the portions of the first conductive gel layer 106*a* penetrating the dielectric material 214 enhance the adhesion of the first conductive gel layer 106*a* to the dielectric material 214.

When the dielectric material 214 is constructed of a non-ceramic material, such as a flexible or non-flexible polymer material, a surface of the polymer material may be treated to enhance adhesion between the first conductive gel layer 106*a* and the dielectric material 214. The use of a polymer in the production of the electrode element 110 may provide crosslinking between the conductive gel element 114 and the polymer of the electrode element 110 during a curing step. Chemical bonding may provide a mechanical connection therebetween that cannot be achieved with electrodes formed of only ceramic materials. Such bonding may aid in maintaining of the conductive gel element 114 on the array for a longer period of time, improved adhesion rate for a longer period of time, improved contact with skin of a patient, reduction of replacement rate of arrays, and/or the like. Examples of manners to treat the polymer material will be described below.

As shown in FIG. 7A, the electrode element 110 is connected to and supported by the flex circuit 102. As shown, the electrode element 110 extends over a portion of the flex circuit 102. The flex circuit 102 is connected to the covering adhesive backed layer 126.

Figure 7B:
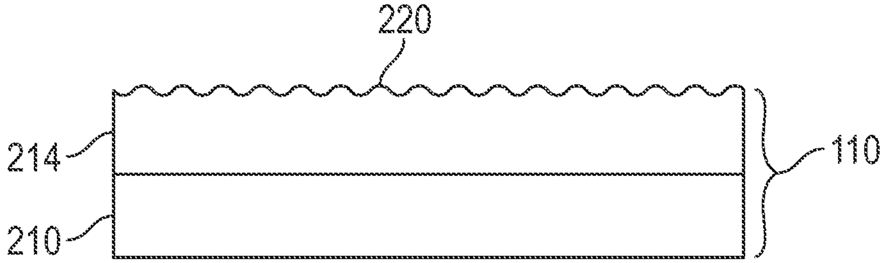
FIG. 7B is a side elevational view of an electrode element provided with a conductive plate and a dielectric material.

Referring now to FIG. 7B, shown therein is the electrode element 110. The electrode element 110 is provided with the conductive plate 210 and the dielectric material 214 as described above. In the example shown in FIG. 7B, the dielectric material 214 is constructed of a non-porous material, such as a polymer. To enhance adhesion with the conductive gel layer 106*a,* the dielectric material 214 is provided with a textured surface 220. The textured surface 220 can be formed by any suitable process, such as abrasion, chemical etching, blasting, grinding, plasma treatment, ozone treatment, and/or the like. The textured surface 220 is spaced a distance away from the conductive plate 210.

Figure 8A:
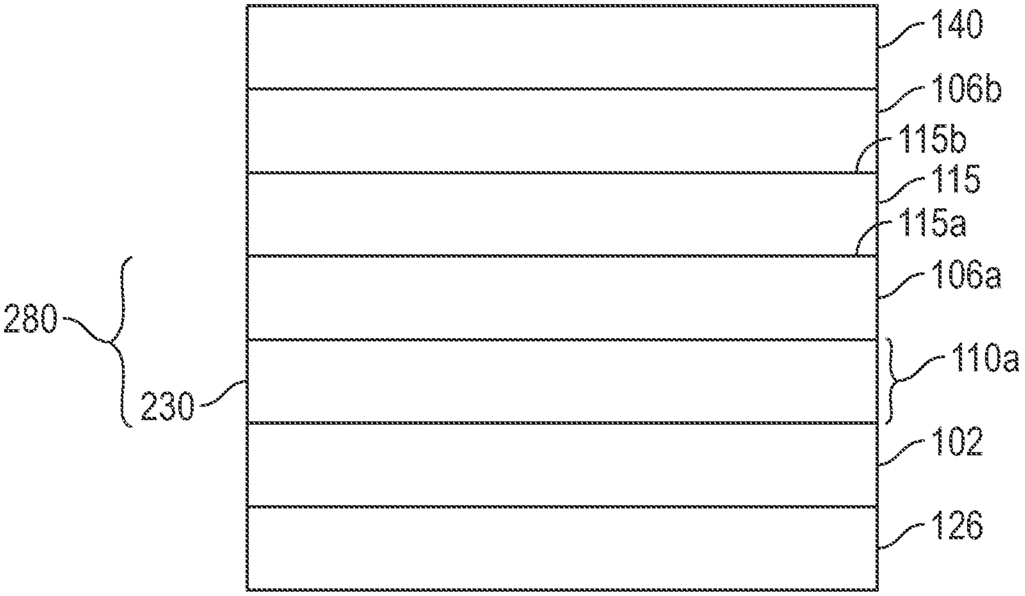
FIG. 8A is a partial schematic view of another embodiment of a transducer array constructed in accordance with the present disclosure.

Referring now to FIG. 8A, shown therein is a partial schematic view of another embodiment of a transducer array 100*a* constructed in accordance with the present disclosure. The transducer array 100*a* is identical in construction and function as the transducer array 100 discussed above, except that the transducer array 100*a* is provided with the plurality of electrode elements 110*a*. FIG. 8A is a cross-sectional view taken across one of the electrode elements 110*a*. The electrode element 110*a* is provided with a conductive layer 230, which is mechanically and electrically connected to the first conductive gel layer 106*a*.

Figure 8B:
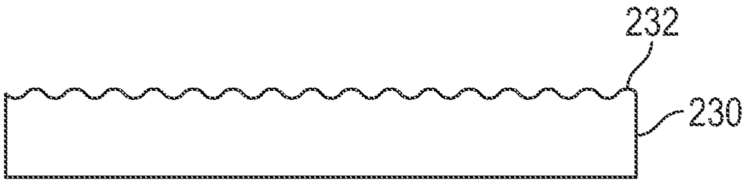
FIG. 8B is a side elevational view of another embodiment of an electrode element provided with a conductive layer having a textured surface.

Referring now to FIG. 8B, shown therein is the electrode element 110*a*. The electrode element 110*a* is provided with the conductive layer 230 as described above. To enhance adhesion with the conductive gel layer 106*a,* the conductive layer 230 is provided with a textured surface 232. The textured surface 232 can be formed by any suitable process, such as abrasion, chemical etching, blasting, grinding, plasma treatment, ozone treatment, and/or the like.

Figure 9:
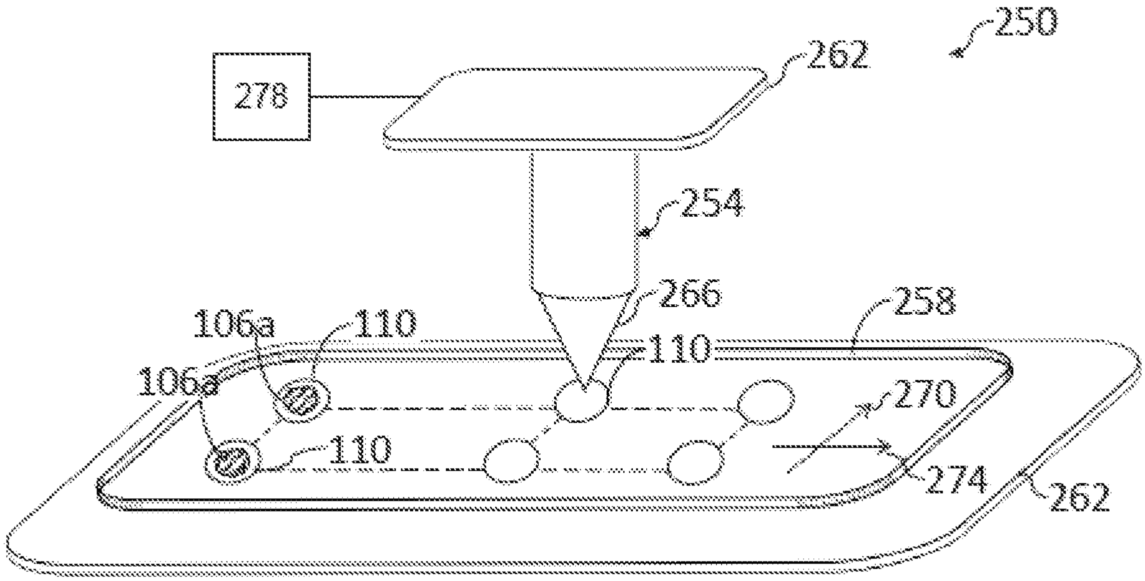
FIG. 9 is an exemplary embodiment of a gel application system constructed in accordance with the present disclosure.

Referring now to FIG. 9, shown therein is a diagram of an exemplary embodiment of a gel application system 250 constructed in accordance with the present disclosure that applies the first conductive gel layer 106*a* and/or the second conductive gel layer 106*b* to the electrode element 110 or 110*a*. The gel application system 250 comprises one or more applicator 254 and a platform 258 moveably attached to a housing 262. Only one applicator 254 is shown for purposes of brevity. It should be understood that multiple applicators 254 can also be used. The one or more applicator 254 further comprises at least a nozzle 266 to eject a conductive gel, described in more detail above. The platform 258 supports a plurality of electrode elements 110 or 110*a* of the transducer arrays 100 or 100*a*. The plurality of electrode elements 110 or 110*a* may be connected to and supported by the flex circuit 102 and/or the cover adhesive-backed layer 126 in the first predetermined pattern discussed above. The cover adhesive-backed layer 126 may engage and be supported by the platform 258. In one embodiment, the applicator 254 may move in one of a first direction 270 or a second direction 274 or a combination of the first direction 270 and the second direction 274. In one embodiment, the platform 258 may move in one of the first direction 270 or the second direction 274 or a combination of the first direction 270 and the second direction 274. In one embodiment, the gel application system 250 includes a controller 278 to control movement of the platform 258 and/or to control movement of the applicator 254.

In one embodiment, the nozzle 266 has an application distance determined by the distance between the nozzle 266 from the platform 258, and ejects conductive gel (in liquid form) at an application pressure, and moves at an application velocity relative to the platform 258. By adjusting the application distance, the application pressure, and the application velocity, the amount of conductive gel applied by the nozzle 266 can be adjusted. The application velocity may be caused by moving the applicator 254 and/or the platform 258 in one of the first direction 270, the second direction 274, or the combination of the first direction 270 and the second direction 274.

In one embodiment, the application pressure is selected such that a portion of the conductive gel is wicked into pores of the dielectric material 214 when the dielectric material 214 is porous, or wicked into the valleys 224 or 236 so that a contact area, that is an area of the electrode element 110 or 110*a* and the first conductive gel layer 106*a* in contact, is increased. For example, it may be desirable to eject conductive gel at a higher pressure to cause the conductive gel to penetrate further into the ceramic material. By increasing penetration into the ceramic material, adhesion between the electrode element 110 and the first conductive gel layer 106*a* may be increased.

In one embodiment, the gel application system 250 ejects conductive gel in a liquid form (e.g., a flowable state) onto the textured surface 220 or 232. Once the gel application system 250 ejects conductive gel onto a particular electrode element 110 or 110*a*, the gel application system 250 may eject conductive gel onto another one or more of the electrode elements 110 or 110*a* until the conductive gel has been applied to all of the electrode elements 110 or 110*a*. Once the conductive gel is applied, the conductive gel is cured on the electrode elements 110 or 110*a*. For example, the liquid conductive gel may be exposed to a UV light emitted by a UV source to cure the liquid conductive gel into a non-flowable state, e.g., polymerized. The polymerized conductive gel may form the first conductive gel layer 106*a*.

In one embodiment, the applicator 254 may be hand-held, that is, the applicator 254 may be held and/or moved by a user instead of being moveably attached to the housing 262. In such an embodiment, the user may use the applicator 254 to eject conductive gel onto the dielectric material 214 of the conductive layer 230.

Once the first conductive gel layer 106*a* is formed, the support layer 115 may be applied to the electrode elements 110 or 110*a*, and then the applicator 254 may be used to apply conductive gel onto the support layer 115 to form the second conductive gel layer 106*b*. As discussed above, the support layer 115 is optional and therefore applying the support layer 115 to the first conductive gel layer 106*a* is also optional.

Figure 10:
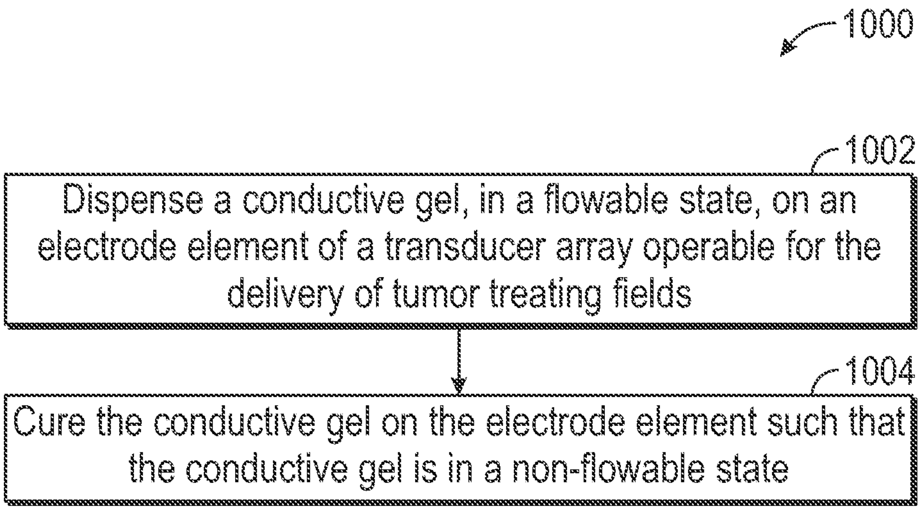
FIG. 10 is a process for making at least one tumor treating field electrode in accordance with the present disclosure.

Shown in FIG. 10 is a process 1000 for making at least one tumor treating field electrode 280 (see FIG. 7A and FIG. 7B). The tumor treating field electrode 280 is a conductive gel assembly. More particularly, at a step 1002, a conductive gel is dispensed, in a flowable state, on one of the electrode elements 110 or 110*a* of the transducer array 100 or 100*a* operable for the delivery of tumor treating fields. Then, at a step 1004, the conductive gel is cured on the electrode element 110 or 110*a* such that the conductive gel is in a non-flowable state.

Figure 11:
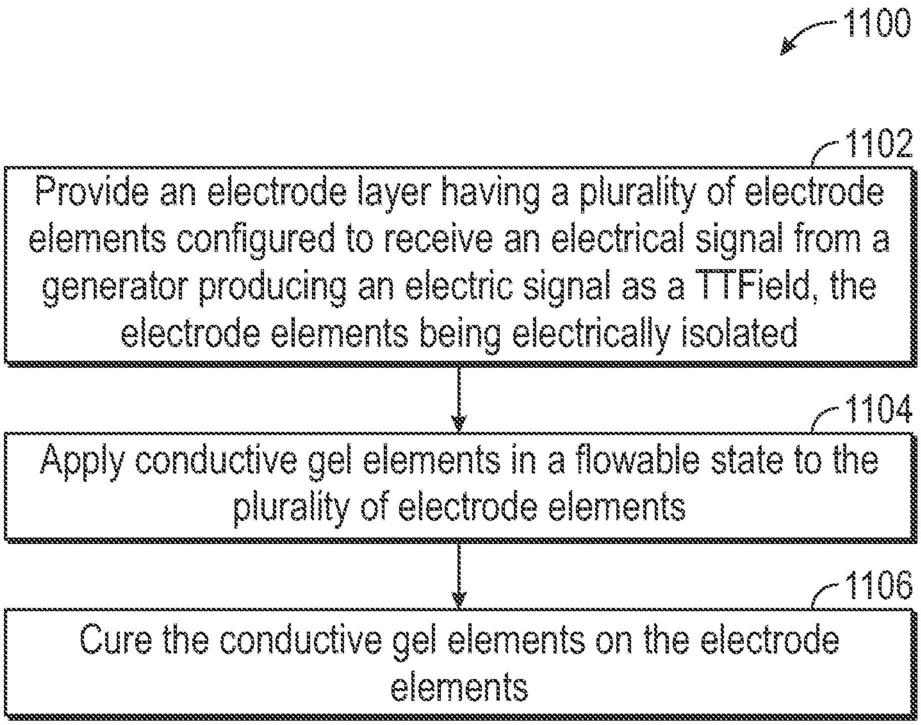
FIG. 11 is a process for making a transducer array in accordance with the present disclosure.

Shown in FIG. 11 is a process 1100 for making the transducer array 100 or 100*a*. In a step 1102, an electrode layer having a plurality of electrode elements 110 or 110*a* configured to receive an electrical signal from an electric field generator producing an electric signal as a TTField is provided. The electrode elements 110 or 110*a* are electrically isolated. In a step 1104, conductive gel elements 114 are applied in a flowable state to the plurality of electrode elements 110 or 110*a*. In a step 1106, the conductive gel elements are cured on the electrode elements.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A method of making at least one tumor treating field (TTField) electrode, comprising:

dispensing a first conductive gel layer, in a flowable state, on an electrode element of a transducer array operable for delivery of tumor treating fields (TTFields) having a frequency from 50 kHz to 1 MHz in response to receiving an electrical signal from an electric field generator;

applying a first side of a support layer onto the first conductive gel layer;

applying a second conductive gel layer, in the flowable state, onto a second side of the support layer, the second conductive gel layer overlapping the first conductive gel layer; and curing the first conductive gel layer and the second conductive gel layer on the electrode element such that each conductive gel layer is in a non-flowable state; and wherein the support layer is a flexible material having a plurality of voids intersecting the first side and the second side, and the second conductive gel layer passes through the voids and bonds the support layer to the first conductive gel layer.

2. The method of claim 1, wherein prior to dispensing the first conductive gel layer, the method further comprises texturing at least a portion of a surface of the electrode element to form a textured surface, and wherein dispensing the first conductive gel layer is further defined as dispensing the first conductive gel layer, in the flowable state, onto the textured surface.

3. The method of claim 2, wherein the electrode element includes a dielectric material having an exterior surface, and wherein the step of texturing at least the portion of the surface of the electrode element is defined further as texturing the exterior surface of the dielectric material.

4. The method of claim 2, wherein the electrode element includes a conductive material having an exterior surface, and wherein the step of texturing at least the portion of the surface of the electrode element is defined further as texturing the exterior surface of the conductive material.

5. The method of claim 1, wherein the electrode element is a first electrode element, and the method further comprising dispensing the first conductive gel layer, in the flowable state, on a second electrode element of the transducer array operable for delivery of tumor treating fields (TTFields); and curing the first conductive gel layer on the second electrode element such that the first conductive gel layer on the second electrode element is in the non-flowable state.

6. The method of claim 5, wherein the support layer is constructed of a non-conductive material.

7. The method of claim 1, wherein the electrode element includes a dielectric material having an exterior surface, the dielectric material being porous.

8. The method of claim 1, further comprising the step of disposing a mold about a surface of the electrode element prior to dispensing the first conductive gel layer, wherein a sidewall of the mold extends beyond the surface of the electrode element and defines a thickness for the first conductive gel layer in the non-flowable state.

9. The method of claim 1, wherein the transducer array comprises at least one barrier formed of a polymer, the barrier associated with and surrounding a perimeter of the electrode element; and, wherein the step of curing the first conductive gel layer and the second conductive gel layer causes cross-linking between the first conductive gel layer and a polymer of the barrier.

10. The method of claim 1, further comprising the step of disposing a quartz plate in at least one of the first conductive gel layer and the second conductive gel layer applied to the electrode element and retaining the quartz plate in position during the step of curing the first conductive gel layer and the second conductive gel layer.

11. A method of making a transducer array for generating tumor treating fields (TTFields) having a frequency from 50 kHz to 1 MHz, comprising:

providing an electrode layer having a plurality of electrode elements configured to generate tumor treating fields (TTFields) having the frequency from 50 kHz to 1 MHz in response to receiving an electrical signal from an electric field generator, the plurality of electrode elements being disposed in a first pattern;

applying conductive gel elements in a flowable state to the plurality of electrode elements, the conductive gel elements including a first conductive gel layer and a second conductive gel layer by applying the first conductive gel layer to the plurality of electrode elements; applying a first side of a support layer onto the first conductive gel layer; and applying the second conductive gel layer, in the flowable state, onto a second side of the support layer in a second pattern corresponding to the first pattern such that the first and second conductive gel layers on each of the plurality of electrode elements overlap; and curing the conductive gel elements on the plurality of electrode elements; and wherein the support layer is a flexible material having a plurality of voids intersecting the first side and the second side, and the second conductive gel layer passes through the voids and bonds the support layer to the first conductive gel layer.

12. The method of claim 11, further comprising:

providing the plurality of electrode elements on a flex circuit; and bonding the first side of the support layer to at least a portion of the flex circuit using a bonding material.

13. The method of claim 11, wherein prior to applying conductive gel elements in the flowable state to the plurality of electrode elements, further comprising:

texturing at least a portion of a surface of the plurality of electrode elements to form a plurality of textured surfaces, wherein applying conductive gel elements in the flowable state is defined further as applying conductive gel elements in the flowable state onto the textured surfaces of the plurality of electrode elements.

14. The method of claim 13, wherein the plurality of electrode elements include a dielectric material having an exterior surface, and texturing at least the portion of the surface of the plurality of electrode elements is defined further as texturing the exterior surfaces of the dielectric materials.

15. The method of claim 13, wherein the plurality of electrode elements include a conductive material having an exterior surface, wherein the texturing at least the portion of the surface of the electrode elements is defined further as texturing the exterior surface of the conductive material.

16. The method of claim 11, wherein the plurality of electrode elements include a dielectric material having an exterior surface, the dielectric material being porous and receiving at least a portion of the conductive gel elements in the flowable state to enhance adhesion between the dielectric material and the conductive gel elements.

17. The method of claim 11, wherein the plurality of electrode elements are electrically isolated.

18. The method of claim 11, wherein the plurality of electrode elements are coated with a dielectric material selected from a ceramic material, a non-flexible polymer, or a flexible polymer film.

19. The method of claim 11, wherein adjacent ones of the plurality of electrode elements have a gap therebetween.

20. A transducer array, comprising:

a plurality of electrode elements in a first pattern, the electrode elements configured to receive electrical signals from an electric field generator to produce a tumor treating field (TTField) having a frequency from 50 kHz to 1 MHz, the plurality of electrode elements forming a plurality of separate conductive regions; and a plurality of isolated conductive gel elements having a second pattern corresponding to the first pattern, a first isolated conductive gel element of the plurality of isolated conductive gel elements being in contact with a first electrode element of the plurality of electrode elements, a second isolated conductive gel element of the plurality of isolated conductive gel elements being in contact with a second electrode element of the plurality of electrode elements, the first isolated conductive gel element and the first electrode element being at least one of capacitively coupled and electrically coupled, the second isolated conductive gel element and the second electrode element being at least one of capacitively coupled and electrically coupled, the plurality of isolated conductive gel elements being in a flowable state, each conductive gel element of the plurality of isolated conductive gel elements includes a first conductive gel layer, a second conductive gel layer, and a support layer disposed between the first conductive gel layer and the second conductive gel layer, the first conductive gel layer and the second conductive gel layer overlapping, and the support layer being a flexible material having a first side, a second side, and a plurality of voids extending from the first side to the second side; and wherein the second conductive gel layer passes through the voids and bonds the support layer to the first conductive gel layer.

21. The transducer array of claim 20, wherein the electrode elements in the plurality of electrode elements have a textured surface, and wherein each of the plurality of isolated conductive gel elements are in contact with the textured surface of a respective one of the plurality of electrode elements.

* * * * *